(12) United States Patent
Chung et al.

(10) Patent No.: US 10,080,775 B2
(45) Date of Patent: Sep. 25, 2018

(54) PEPTIDE HAVING SKIN WHITENING ACTIVITY, AND USE THEREOF

(71) Applicant: CAREGEN CO., LTD., Gyeonggi-do (KR)

(72) Inventors: Yong Ji Chung, Gyeonggi-do (KR); Eun Mi Kim, Gyeonggi-do (KR); Eung-Ji Lee, Gyeonggi-do (KR); Jan Di Kim, Seoul (KR)

(73) Assignee: CAREGEN CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/553,693

(22) PCT Filed: Feb. 6, 2017

(86) PCT No.: PCT/KR2017/001315
§ 371 (c)(1),
(2) Date: Aug. 25, 2017

(87) PCT Pub. No.: WO2017/105161
PCT Pub. Date: Jun. 22, 2017

(65) Prior Publication Data
US 2018/0042981 A1    Feb. 15, 2018

(51) Int. Cl.
*A61K 38/00* (2006.01)
*A61K 8/64* (2006.01)
(Continued)

(52) U.S. Cl.
CPC ............ *A61K 38/005* (2013.01); *A61K 38/02* (2013.01); *A61Q 19/02* (2013.01); *A61K 8/00* (2013.01)

(58) Field of Classification Search
CPC ...... A61K 38/00; A61K 38/1841; A61K 8/64; A61Q 19/02; C07K 14/495; C07K 7/08
(Continued)

(56) References Cited

U.S. PATENT DOCUMENTS

| | | | |
|---|---|---|---|
| 8,969,296 B2* | 3/2015 | Chung | A61K 8/64 424/62 |
| 2010/0160238 A1* | 6/2010 | Chung | A61K 8/64 514/8.9 |

(Continued)

FOREIGN PATENT DOCUMENTS

| | | |
|---|---|---|
| EP | 2990027 A1 | 3/2016 |
| JP | 2001-002527 | 1/2001 |

(Continued)

OTHER PUBLICATIONS

Peng et al, "Synthesis and activity of tumor-homing peptide iRGD and histone deacetylase ihibitor valproic acid conjugate," Bioorganic & Medicinal Chemistry Letters, 2014, 24: 1928-1933.*

(Continued)

*Primary Examiner* — Julie Ha
(74) *Attorney, Agent, or Firm* — Harness, Dickey & Pierce, P.L.C.

(57) ABSTRACT

A peptide having skin-whitening activity is described. The peptide exhibits an excellent skin whitening effect by inhibiting melanogenesis, inhibiting the activity of tyrosinase, inhibiting the expression of melanosis-involved factors, and inhibiting melanosome transfer. The peptide has excellent skin permeability due to the small size thereof. Excellent activity and stability of the foregoing peptide can be very favorably applied to cosmetics.

18 Claims, 23 Drawing Sheets

Specification includes a Sequence Listing.

(51) Int. Cl.
  *A61Q 19/02* (2006.01)
  *A61Q 7/00* (2006.01)
  *A61Q 7/02* (2006.01)
  *C07K 7/08* (2006.01)
  *C07K 14/00* (2006.01)
  *A61K 38/02* (2006.01)
  *A61K 8/00* (2006.01)

(58) Field of Classification Search
  USPC ......... 530/326, 327, 328; 514/8.9, 16.7, 1.9; 424/62
  See application file for complete search history.

(56) References Cited

U.S. PATENT DOCUMENTS

2017/0073389 A1  3/2017  Hahn et al.
2017/0246098 A1  8/2017  Raposo et al.

FOREIGN PATENT DOCUMENTS

| JP | 2010-524920 A | 7/2010 |
| KR | 10-0840144 | 6/2008 |
| KR | 10-0879239 | 1/2009 |
| KR | 10-1001156 | 12/2010 |
| KR | 10-2015-0119741 | 10/2015 |
| WO | WO-2014/074555 A1 | 5/2014 |
| WO | WO-2016/085208 A1 | 6/2016 |

OTHER PUBLICATIONS

International Search Report (ISR) in PCT/KR2017/001315, dated Jun. 2, 2017, published in WO 2017/105161 and its English translation.
Office Action from corresponding Korean Application No. 10-2015-0182070 dated May 12, 2017 and its English translation.
Extended European Search Report from corresponding European Patent Application No. 17730342.7, dated Jul. 3, 2018.
Office Action from corresponding Japanese Patent Application No. 2017-545262, dated Jul. 3, 2018, and it's English translation.

* cited by examiner

Control

SEQ ID NO: 1

Control

SEQ ID NO: 1

Control

SEQ ID NO. 1

Control

SEQ ID NO: 1

Control

SEQ ID NO: 1

Control

SEQ ID NO. 1

PEPTIDE HAVING SKIN WHITENING ACTIVITY, AND USE THEREOF

TECHNICAL FIELD

The present invention relates to a peptide having a skin-whitening activity and a composition for skin whitening containing the same as an active ingredient.

BACKGROUND ART

Transforming growth factor beta 1 (TGF-β1) is a factor that induces the development of tissues or the maintenance of homeostasis through the control of growth, differentiation, and apoptosis in various types of cells. Transforming growth factor beta 1 has been known to exhibit a melanogenesis inhibitory effect in melanocytes (THE JOURNAL OF BIOLOGICAL CHEMISTRY Vol. 272, No. 7, Issue of February 14, pp. 3967-3972, 1997).

The transforming growth factor beta 1 is shown to function to increase the degradation of tyrosinase, which is an enzyme important for melanogenesis. In addition, the transforming growth factor beta 1 often inhibits melanogenesis by promoting the activity of ERK1/2, which promotes the degradation of microphthalmia-associated transcription factor (MITF), which is a transcription factor that regulates the expression of melanogenesis-involved enzymes, such as tyrosinase, tyrosinase-associated gene-1, and tyrosinase-associated gene-2.

The present inventors, through prior studies, have developed a peptide based on a portion of the amino acid sequence of the transforming growth factor beta 1, and have verified the whitening effect of the peptide in melanocytes. Thereafter, the present inventors have researched structural improvement through binding with various chemical compounds in order to maximize the functions of the peptide, and have found a material of the present invention having an improved whitening effect compared with existing peptides through an effect screening process.

Throughout the entire specification, many papers and patent documents are referenced and their citations are represented. The disclosures of the cited papers and patent documents are entirely incorporated by reference into the present specification, and the level of the technical field within which the present invention falls and the details of the present invention are thus explained more clearly.

DETAILED DESCRIPTION

Technical Problem

The present inventors have endeavored to develop a peptide having excellent skin-whitening activity. As a result, the present inventors have established that a peptide consisting of a peptide having valproic acid bound to the N-terminus of the amino acid sequence of SEQ ID NO: 1 exhibits an excellent skin-whitening effect by inhibiting melanogenesis, inhibiting the activity of tyrosinase and inhibiting the expression of melanogenesis-associated factors, and thus the present inventors have completed the present invention.

Therefore, an aspect of the present invention is to provide a peptide having skin-whitening activity, the peptide consisting of a peptide having valproic acid bound to the N-terminus of the amino acid sequence of SEQ ID NO: 1.

Another aspect of the present invention is to provide a composition for skin whitening, the composition containing the peptide.

Still another aspect of the present invention is to provide a use of the peptide for skin whitening.

Still another aspect of the present invention is to provide a method for skin whitening using the peptide.

Other purposes and advantages of the present invention will become more obvious with the following detailed description of the invention, claims and drawings.

Technical Solution

The present inventors have endeavored to develop a peptide having excellent skin-whitening activity. As a result, the present inventors have established that a peptide consisting of a peptide having valproic acid bound to the N-terminus of the amino acid sequence of SEQ ID NO: 1 exhibits an excellent skin-whitening effect by inhibiting melanogenesis, inhibiting the activity of tyrosinase and inhibiting the expression of melanogenesis-associated factors.

Hereinafter, the present invention will be described in detail.

An aspect of the present invention is to provide a peptide having skin-whitening activity, the peptide consisting of a peptide having valproic acid bound to the N-terminus of the amino acid sequence of SEQ ID NO: 1.

According to an embodiment of the present invention, the peptide inhibits melanogenesis, inhibits the activity and expression of tyrosinase, inhibits the expression of MITF and PAR2, which are factors involved in melanogenesis, inhibits the phosphorylation of CREB, which is a signaling material involved in melanogenesis, inhibits melanosome transfer involved in skin whitening, and promotes melanosome degradation. In addition, the peptide of the present invention inhibits hair growth. These results indicate that the peptide of the present invention has an excellent effect in skin whitening.

As used herein, the term "peptide" refers to a linear molecule formed by allowing amino acid residues to be joined to each other via peptide bonds. The peptide of the present invention may be prepared by chemical synthesis methods known in the art, especially, solid-phase synthesis techniques (Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)) or liquid-phase synthesis techniques (U.S. Pat. No. 5,516,891).

The peptide of the present invention may select a partial region of the amino acid sequence and induce a modification at the N-terminal and/or C-terminal thereof in order to increase the activity thereof.

For example, the C-terminal of the peptide may be modified with a hydroxyl group (—OH), an amino group (—NH₂), an azide (—NHNH₂) or the like, but is not limited thereto.

In addition, a protective group selected from the group consisting of an acetyl group, a fluorenyl methoxy carbonyl group, a formyl group, a palmitoyl group, a myristyl group, a stearyl group and polyethylene glycol (PEG) may be bound to the N-terminal of the peptide.

Such a modification of the N-terminal and/or the C-terminal increases the half-life of the peptide of the present invention, leading to a high half-life for the in vivo administration, thereby greatly improving the stability of the peptide.

As used herein, the term "stability" refers to storage stability (e.g., room-temperature storage stability) as well as in vivo stability. The foregoing protective group protects the peptide of the present invention from attack by protein cleavage enzymes in vivo.

An aspect of the present invention is directed to a composition for skin whitening, the composition containing a peptide consisting of a peptide having valproic acid bound to the N-terminus of the amino acid sequence of SEQ ID NO: 1 as an active ingredient.

Since the composition for skin whitening of the present invention contains the peptide of the present invention as an active ingredient, the description of overlapping contents therebetween will be omitted to avoid excessive complexity of the present specification.

The composition for skin whitening of the present invention can be prepared as a cosmetic composition.

The cosmetic composition may be prepared in any dosage form that is ordinarily prepared in the art. For example, the cosmetic composition may be formulated as a solution, suspension, emulsion, paste, gel, cream, lotion, powder, soap, surfactant-containing cleanser, oil, powder foundation, emulsion foundation, wax foundation, spray, or the like, and more specifically, in the dosage form of an emollient lotion, nourishing lotion, nourishing cream, massage cream, essence, eye cream, cleansing cream, cleansing foam, cleansing water, pack, spray and/or powder, but is not limited thereto.

In cases where the dosage form of the cosmetic composition is a paste, a cream or a gel, useful examples of the carrier ingredient may be an animal oil, a plant oil, wax, paraffin, starch, tracant, a cellulose derivative, polyethylene glycol, silicone, bentonite, silica, talc and/or zinc oxide.

In cases where the dosage form of the cosmetic composition is a power or a spray, useful examples of the carrier component may be lactose, talc, silica, aluminum hydroxide, calcium silicate and/or polyamide powder.

In cases where the dosage form of the cosmetic composition is a spray, the spray may further contain a propellant, such as chlorofluorohydrocarbon, propane, butane and/or dimethyl ether.

In cases where the dosage form of the cosmetic composition is a solution or an emulsion, useful examples of the carrier ingredient may be a solvent, a solubilizer, and/or an emulsifier, and for example, water, ethanol, isopropanol, ethyl carbonate, ethyl acetate, benzyl alcohol, benzyl benzoate, propylene glycol, 1,3-butyl glycol oil, glycerol fatty ester, polyethylene glycol and/or fatty acid esters of sorbitan may be used, but are not limited thereto.

In cases where the dosage form of the cosmetic composition is a suspension, useful examples of the carrier ingredient may be a liquid diluent (such as water, ethanol and/or propylene glycol), a suspending agent (such as ethoxylated isostearyl alcohol, polyoxyethylene sorbitol ester and/or polyoxyethylene sorbitan ester), microcrystalline cellulose, aluminum metahydroxide, bentonite, agar and/or tragacanth, but are not limited thereto.

In cases where the dosage form of the cosmetic composition is a surfactant-containing cleanser, useful examples of the carrier ingredient may be aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives and/or ethoxylated glycerol fatty acid ester, but are not limited thereto.

The ingredients contained in the cosmetic composition of the present invention may include, in addition to the carrier ingredient and the peptide consisting of a peptide having valproic acid bound to the N-terminus of the amino acid sequence of SEQ ID NO: 1 as an active ingredient, ingredients ordinarily used in cosmetic compositions, for example, ordinary supplements, such as an antioxidant, a purifier, a solubilizer, vitamins, a pigment and/or a flavoring agent, but are not limited thereto.

Advantageous Effects

The present invention is directed to a peptide having skin-whitening activity and to a composition for skin whitening containing the same as an active ingredient, and the peptide inhibits melanogenesis, inhibits the activity of tyrosinase, inhibits the expression of melanogenesis-involved factors, and inhibits melanosome transfer, thereby exhibiting an excellent skin-whitening effect. In addition, the peptide has excellent skin permeability due to the small size thereof, and can be very favorably applied to cosmetics due to the excellent activity and stability thereof.

MODE FOR CARRYING OUT THE INVENTION

Figure 1:
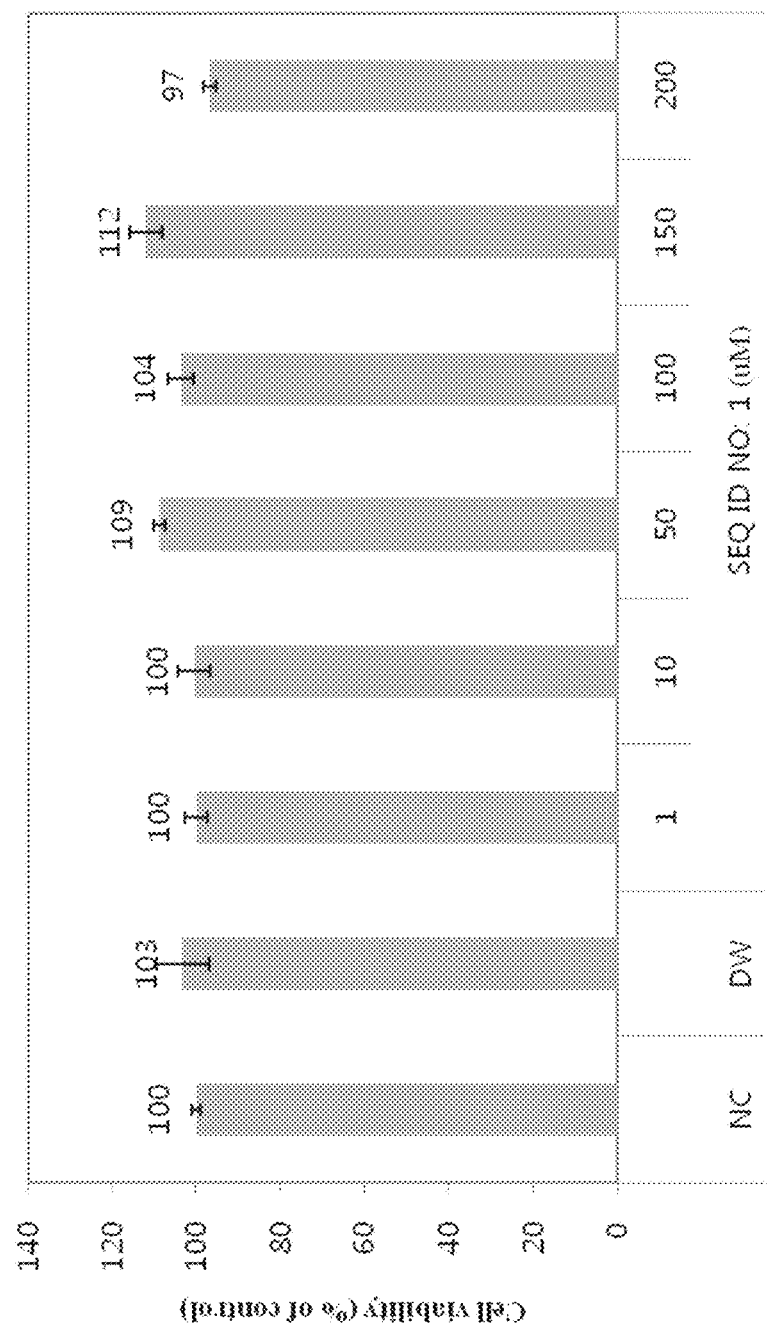
FIG. 1 is a graph showing results of evaluation of the cytotoxicity of a peptide according to an embodiment of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis

Into a reaction container, 700 mg of chloro trityl chloride resin (CTL resin, Nova Biochem Cat No. 01-64-0021) was placed, and 10 ml of methylene chloride (MC) was added, followed by stirring for 3 minutes. Thereafter, the solution was removed, 10 ml of dimethylform amide (DMF) was added, followed by stirring for 3 minutes, and then the solvent was again removed. Into a reactor, 10 ml of a dichloromethane solution was placed, and 200 mmole Fmoc-Asp(OtBu)-OH (Bachem, Swiss) and 400 mmole diisopropyl ethylamine (DIEA) were added. The mixture was thoroughly dissolved with stirring, and the reaction was conducted with stirring for 1 hour. After the reaction, the resulting material was washed, and methanol and DIEA (2:1) were dissolved in dichloromethane (DCM), followed by reaction for 10 minutes, and then the resulting material was washed with excess DCM/DMF (1:1). After the solution was removed, 10 ml of dimethylform amide (DMF) was added, followed by stirring for 3 minutes, and then the solvent was again removed. Into a reaction container, 10 ml of a deprotection solution (20% piperidine/DMF) was placed, followed by stirring at room temperature for 10 minutes, and then the solution was removed. An equal amount of a deprotection solution was added, and then the reaction was again allowed to continue for 10 minutes, followed by removal of the solution. The resulting material was washed twice with DMF, once with MC, and once with DMF, for 3 minutes each, thereby preparing Asp-CTL resin. Into a new reactor, 10 ml of a DMF solution was placed, and 200 mmol Fmoc-Gly-OH (Bachem, Swiss), 200 mmol HoBt, and 200 mmole Bop were added, and the mixture was thoroughly dissolved with stirring. Into a reactor, 400 mmole DIEA was added in two portions, and then stirring was conducted for at least 5 minutes until all solids were dissolved. The dissolved amino acid mixed solution was placed in the reactor containing the deprotected resin, and the reaction was conducted with stirring at room temperature for 1 hour. After the reaction liquid was removed, stirring was conducted using a DMF solution three times for 5 minutes each time, followed by removal of the DMF solution. A small amount of the reaction resin was taken to check the extent of the reaction using the Kaiser test (Ninhydrin test). Using the deprotection solution, the deprotection reaction was conducted twice in the same manner as described above to prepare Gly-Asp-CTL resin. After sufficient washing with DMF and MC, the Kaiser test was again conducted, and then the following amino acid attachment test was conducted in the same manner as described above. Based on the selected amino acid sequence, a chain reaction was carried out in the order of Fmoc-Arg(Pbf)-OH, Fmoc-Gly-OH, Fmoc-Gly-OH, Fmoc-Tyr(tBu)-OH, Fmoc-Gln(Trt)-OH, Fmoc-Thr(tBu)-OH, Fmoc-Asp(OtBu)-OH, Fmoc-Leu-OH, Fmoc-Ser(tBu)-OH, Fmoc-Trp-OH, and Fmoc-Ile-OH. The Fmoc-protective group was reacted twice with a deprotection solution for 10 minutes for each time, and then washed thoroughly. Thereafter, the activated valproic acid was bound, and then the prepared peptidyl resin was washed three times with DMF, MC, and methanol for each time, dried under slow-flowing nitrogen gas, and completely dried by vacuum-drying under $P_2O_5$. Then, 30 ml of a missing solution (81.5% trifluoroacetic acid (TFA), 5% distilled water, 5% thioanisole, 5% phenol, 2.5% EDT, and 1% TIS) was added, and the reaction was allowed to continue for 2 hours while the mixture was intermittently stirred at room temperature. The resin was obtained through filtration, and the resin was washed with a small amount of a TFA solution, and then mixed with the stock solution. The distillation was conducted under reduced pressure to leave about half of the total volume, and then 50 ml of cold ether was added to induce precipitation. Thereafter, the precipitate was collected by centrifugation, followed by washing twice with cold ether. The stock solution was removed, and the precipitate was sufficiently dried under nitrogen, to synthesize 0.8 g of Valprooyl-Ile-Trp-Ser-Leu-Asp-Thr-Gln-Tyr-Gly-Gly-Arg-Gly-Asp-COOH, peptide 1 (SEQ ID No. 1) before purification (yield: 89.0%). The molecular weight of the peptide was found to be 1593.7 (theoretical value: 1593.7) when measured using a molecular weight meter.

TABLE 1

| SEQ ID NO | Amino acid sequence (5'→3') | Analytical value (mass spectrometer) | |
|---|---|---|---|
| | | Analytical value | Theoretical value |
| 1 | VC-IWSLDTQYGGRGD | 1593.7 | 1593.7 |

Example 1: Cytotoxicity Test

After melanin-forming cells (B16F10 cell line) dispensed in 48-well culture plates were incubated in a 37° C. incubator for 24 hours, the medium for each plate was removed and replaced with serum-free medium, and then the cells were treated with the peptide of the present invention at different concentrations (1, 10, 50, 100, 150, 200 uM). After the cells were incubated for 72 hours, the MTT reagent was added, followed by reaction for 4 hours. Then, the generated formazan was dissolved in DMSO, and the absorbance was measured at 560 nm.

As a result of performing the MTT assay to examine whether the cytotoxicity of the peptide consisting of a peptide having valproic acid bound to the N-terminus of the amino acid sequence of SEQ ID NO: 1 on melanocytes, it was verified that no cytotoxicity was observed in the groups treated with 1 uM to 200 uM (FIG. 1).

Example 2: Measurement of Melanin Production

After melanin-forming cells (B16F10 cell line) dispensed in 6-well culture plates were incubated in a 37° C. incubator for 24 hours, the medium for each plate was removed and then replaced with new medium (2% serum medium). Then, the cells were treated with α-MSH (200 ng/ml), arbutin (200, 500 uM), or the peptide of the present invention at different concentrations (50, 100, 200 uM). Thereafter, the cells were incubated for 72 hours, and then the culture medium was removed. The cells were detached and then transferred into a 1.5 ml tube, followed by centrifugation at 13,000 rpm for 3 minutes. The supernatant was removed, and cell pellets were collected to observe melanin. Then, 150 µl of 2 M NaOH was added to the cell pellets to lyse intracellular melanin at 60° C. for 30 minutes. Then, 100 µl of the supernatant obtained from the lysis was added into each well of a 96-well plate, and the absorbance at 490 nm was measured. The results are shown in FIGS. 2a and 2b.

Figure 2A:
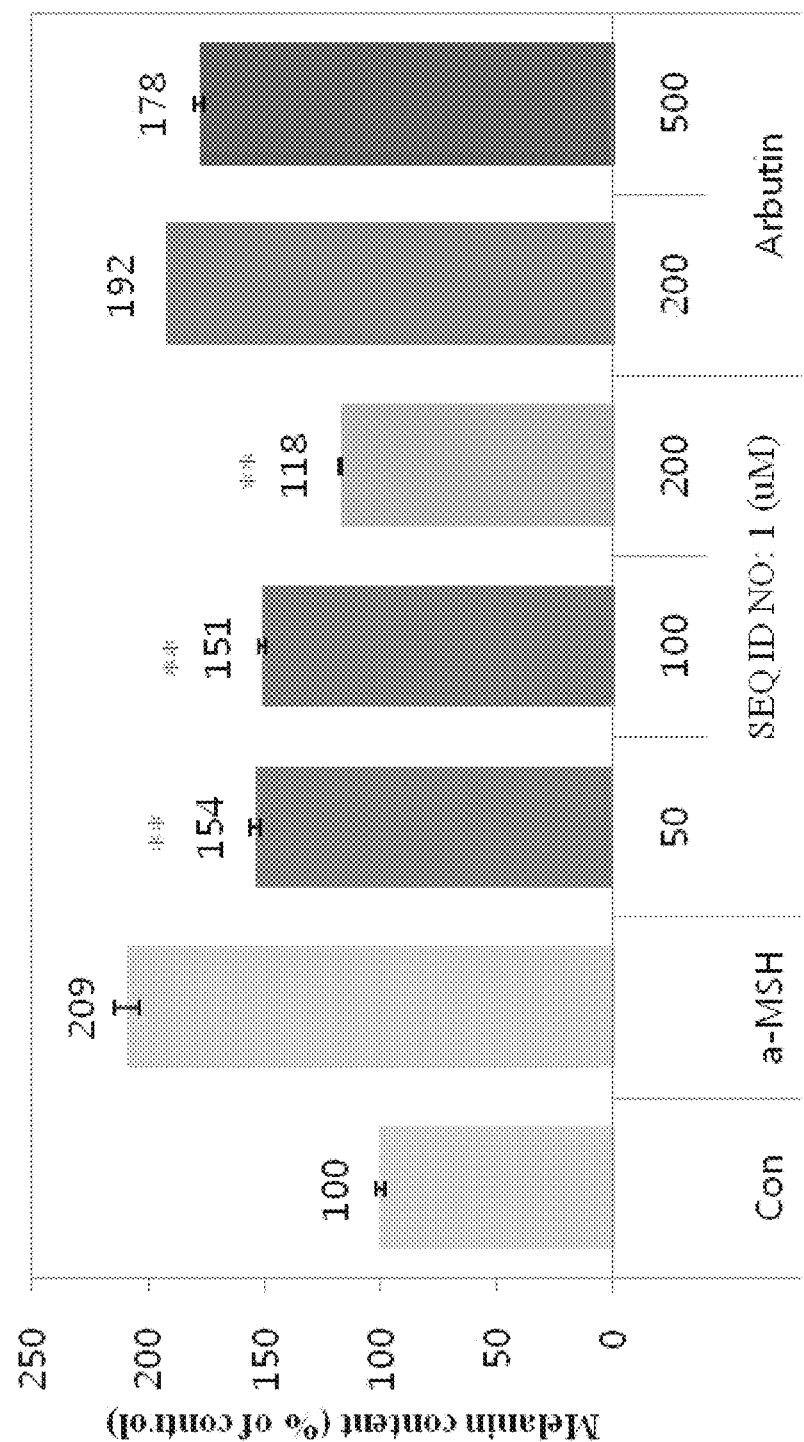
FIG. 2a is a graph showing results of measurement of melanin production when melanoma cell line (B16F10) was treated with a peptide according to an embodiment of the present invention.
Figure 2B:
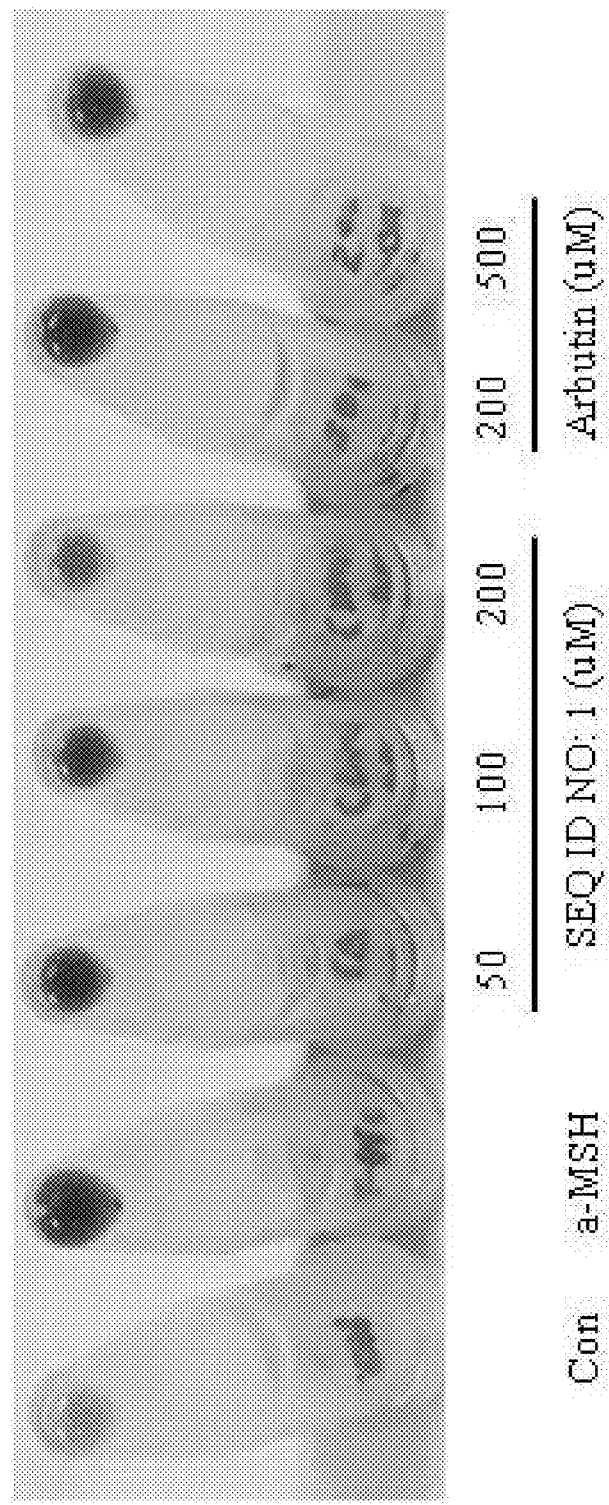
FIG. 2b is an image showing results of measurement of melanin production when melanoma cell line (B16F10) was treated with a peptide according to an embodiment of the present invention.

As can be seen from FIGS. 2a and 2b, the melanogenesis inhibitory effect of the peptide consisting of a peptide having valproic acid bound to the N-terminus of the amino acid sequence of SEQ ID NO: 1 in a dose-dependent manner was verified (**$P \leq 0.01$).

Example 3: Visual Observation of Melanin Production

After melanin-forming cells (B16F10 cell line) dispensed in 6-well culture plates were incubated in a 37° C. incubator for 24 hours, the medium for each plate was removed and replaced with new medium (10% serum medium). Then, the cells were treated with α-MSH (200 ng/ml), arbutin (500 uM), or the peptide of the present invention at different concentrations (50, 100, 200 uM). The cells were incubated for 72 hours, and then the formed melanin was observed through an optical microscope. The results are shown in FIG. 3.

Figure 3:
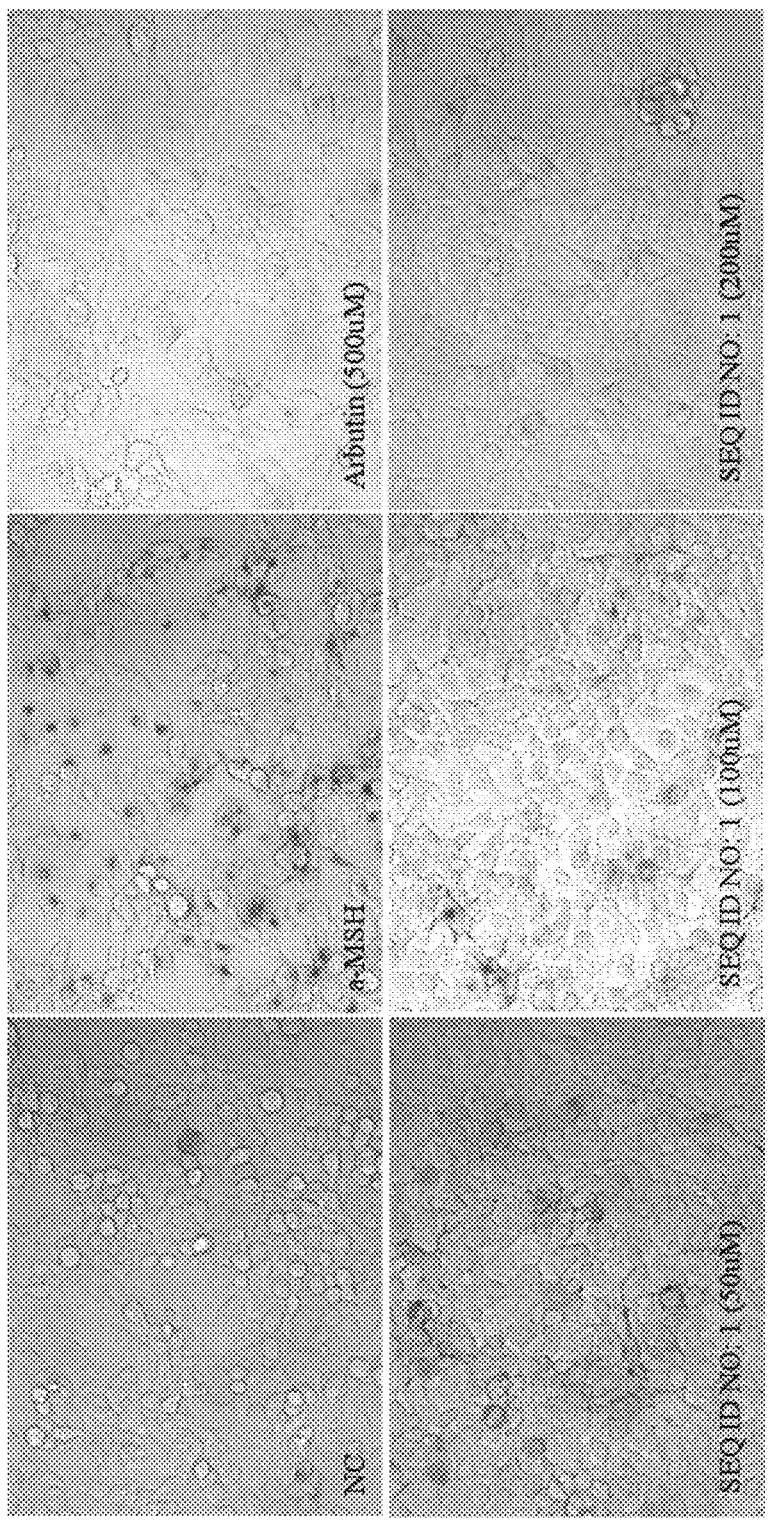
FIG. 3 provides images showing results of observation of melanogenesis when melanoma cell line (B16F10) was treated with a peptide according to an embodiment of the present invention.

As can be seen from FIG. 3, the melanogenesis inhibitory effect of the peptide consisting of a peptide having valproic acid bound to the N-terminus of the amino acid sequence of SEQ ID NO: 1 in a dose-dependent manner was verified through cell morphology.

Example 4: Measurement of Intercellular Tyrosinase Activity

Melanoma cells (B16F10) were incubated in 6-well culture plates, and then the cells were treated with α-MSH (200 ng/ml), the peptide at different concentrations (50, 100, 200 uM), or arbutin (200, 500 uM) as a positive control, followed by incubation for 72 hours. The 6-well culture plates were loaded on ice and washed with cool PBS, and then 300 µl of 0.1 M sodium phosphate buffer (pH 6.8 lysis buffer) containing 1% Triton X-100 was added. The cells were collected in a 1.5 mL tube, and then cell membranes were disrupted by repeating rapid-freezing at −270° C. and thawing, five times. Then, the tube was centrifuged at 13,000 rpm for 20 minutes, and then the supernatant was collected in another 1.5 mL tube, and the protein content of the samples was quantified. The samples were diluted to have the same protein concentration and then dispensed in three wells each in a 96-well culture plate, and then 20 µl of 1 0 mM L-dopa was added, followed by incubation at 37° C. for 1 hour. The absorbance was measured at 475 nm, and the results are shown in FIG. 4.

Figure 4:
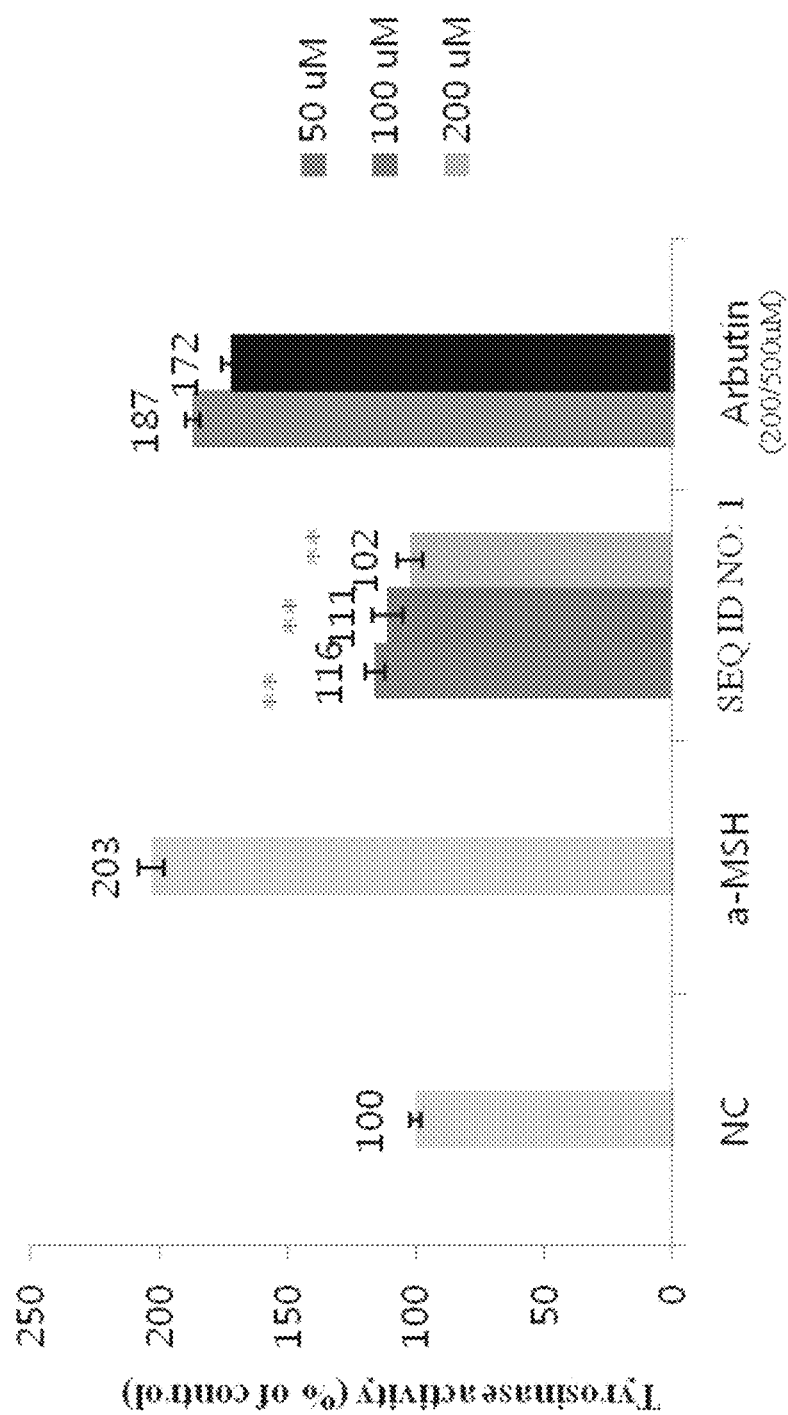
FIG. 4 is a graph showing results of measurement of tyrosinase activity in cells when melanoma cell line (B16F10) was treated with a peptide according to an embodiment of the present invention.

As can be seen from FIG. 4, the tyrosinase activity inhibitory effect of the peptide consisting of a peptide having valproic acid bound to the N-terminus of the amino acid sequence of SEQ ID NO: 1 in a dose-dependent manner was verified (**$P \leq 0.01$).

Example 5: Measurement of Tyrosinase Expression Level

After melanin-forming cells (B16F10 cell line) dispensed in 6-well culture plates were incubated in a 37° C. incubator for 24 hours, the medium for each plate was removed and replaced with new medium (10% serum medium). Then, the cells were treated with α-MSH (200 ng/ml) or the peptide of the present invention at different concentrations (50, 100 uM). Then, the cells were incubated for 48 hours, and the intracellular expression protein was stained with tyrosinase antibody (Santa Cruz biotechnology, USA) and FITC-conjugated secondary IgG antibody (Santa Cruz biotechnology, USA). The expression level thereof was visually observed through a fluorescence microscope, and the results are shown in FIG. 5.

Figure 5:
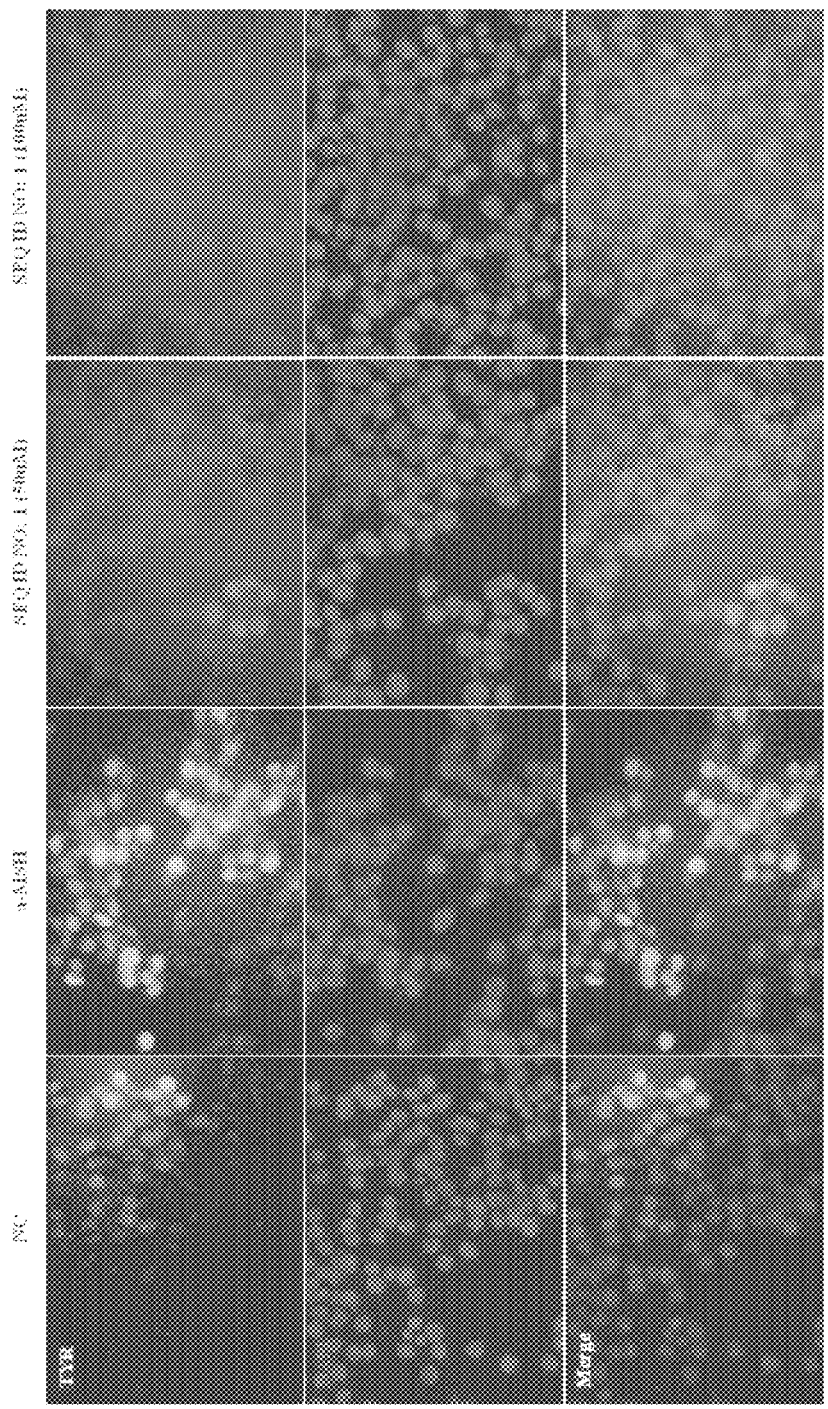
FIG. 5 provides images showing results of confirming the tyrosinase expression level in cells using tyrosinase antibody when melanoma cell line (B16F10) was treated with a peptide according to an embodiment of the present invention.

As can be seen from FIG. 5, the tyrosinase expression inhibitory effect of the peptide consisting of a peptide having valproic acid bound to the N-terminus of the amino acid sequence of SEQ ID NO: 1 in a dose-dependent manner was verified.

Example 6: Observation of Change in Gene Expression of Melanin-Forming Factors After melanin-forming cells (B16F10 cell line) were incubated in 6-well culture plates for 24 hours, the cells were treated with α-MSH (200 ng/ml), arbutin (500 uM), or the present peptide at different concentrations (100, 200 uM). After RNA was extracted from the cells incubated for 24 hours, cDNA was prepared. Then, PCR was conducted using the primers shown in Table 2 below, which are specific to MITF and tyrosinase, respectively, as melanogenesis-involved factors, and then the change in the expression of each gene was observed. The results are shown in FIG. 6.

TABLE 2

| SEQ ID NO | Name | Sequence listing (5'→3') | Note |
|---|---|---|---|
| 2 | MITF_F | CCAGCCTGGCGAT CATGTCAT | Annealing temperature, 60° C. |
| 3 | MITF_R | GGTCTGGACAGGA GTTGCTG | |
| 4 | Tyrosinase_F | GGCCAGCTTTCAG GCAGAGG | Annealing temperature, 60° C. |
| 5 | Tyrosinase_R | TGGTGCTTCATGG GCAAAAT | |

Figure 6:
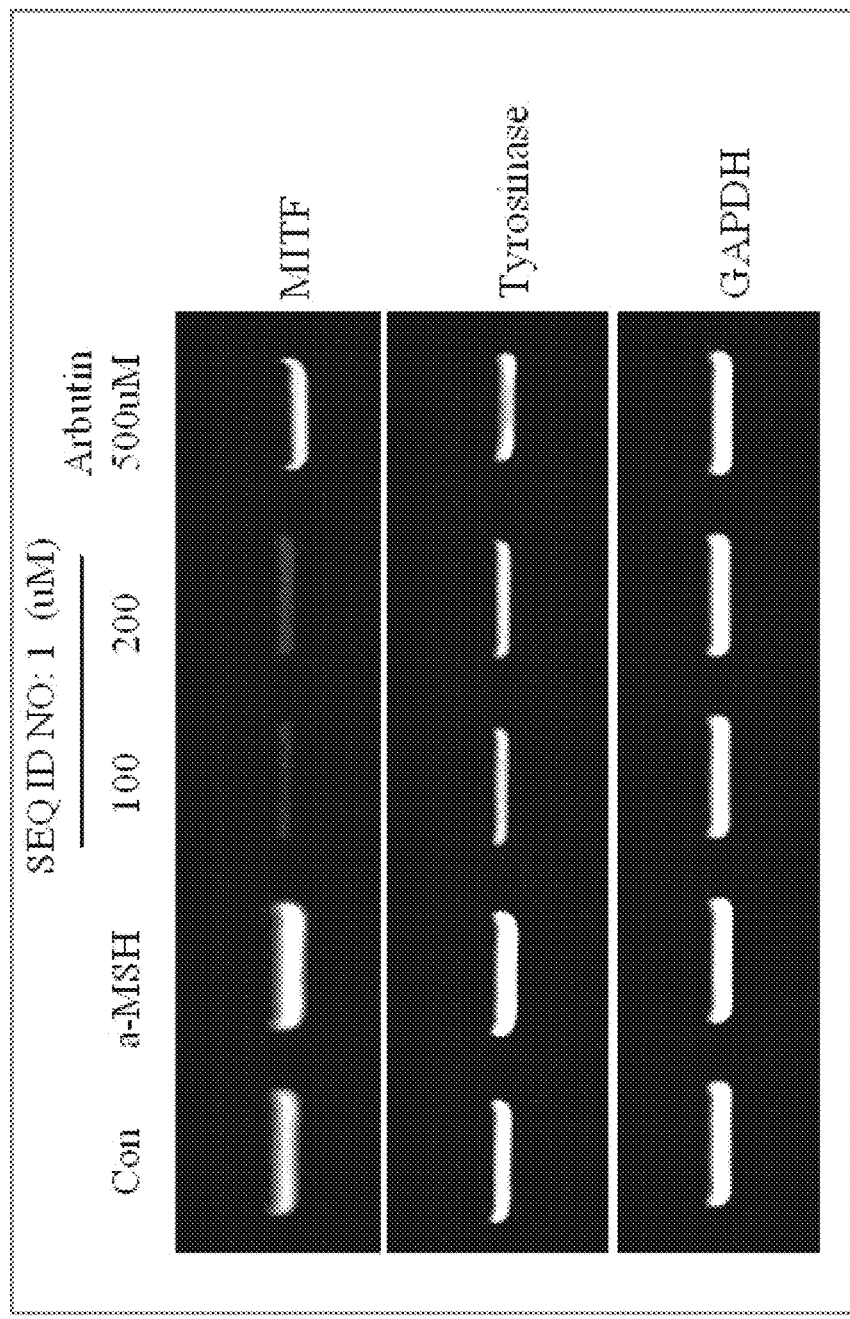
FIG. 6 provides images showing PCR results of confirming the gene expression change of melanogenesis factors when melanoma cell line (B16F10) was treated with a peptide according to an embodiment of the present invention.

As can be seen from FIG. 6, it was verified that the peptide consisting of a peptide having valproic acid bound to the N-terminus of the amino acid sequence of SEQ ID NO: 1 had strong effects of inhibiting MITF and tyrosinase genes.

Example 7: Observation of Change in Protein Expression of Melanin-Forming Factors After melanin-forming cells (B16F10 cell line) were incubated in 6-well culture plates for 24 hours, the cells were treated with α-MSH (200 ng/ml) or the present peptide at different concentrations (50, 100 uM). After the cells were incubated for 72 hours, the cells were lysed, and the expression of MITF (Santa Cruz Biotechnology, USA) and tyrosinase (Santa Cruz Biotechnology, USA), which are core factors involved in melanogenesis, was observed using a western blot method using specific antibodies. The results are shown in FIG. 7.

Figure 7:
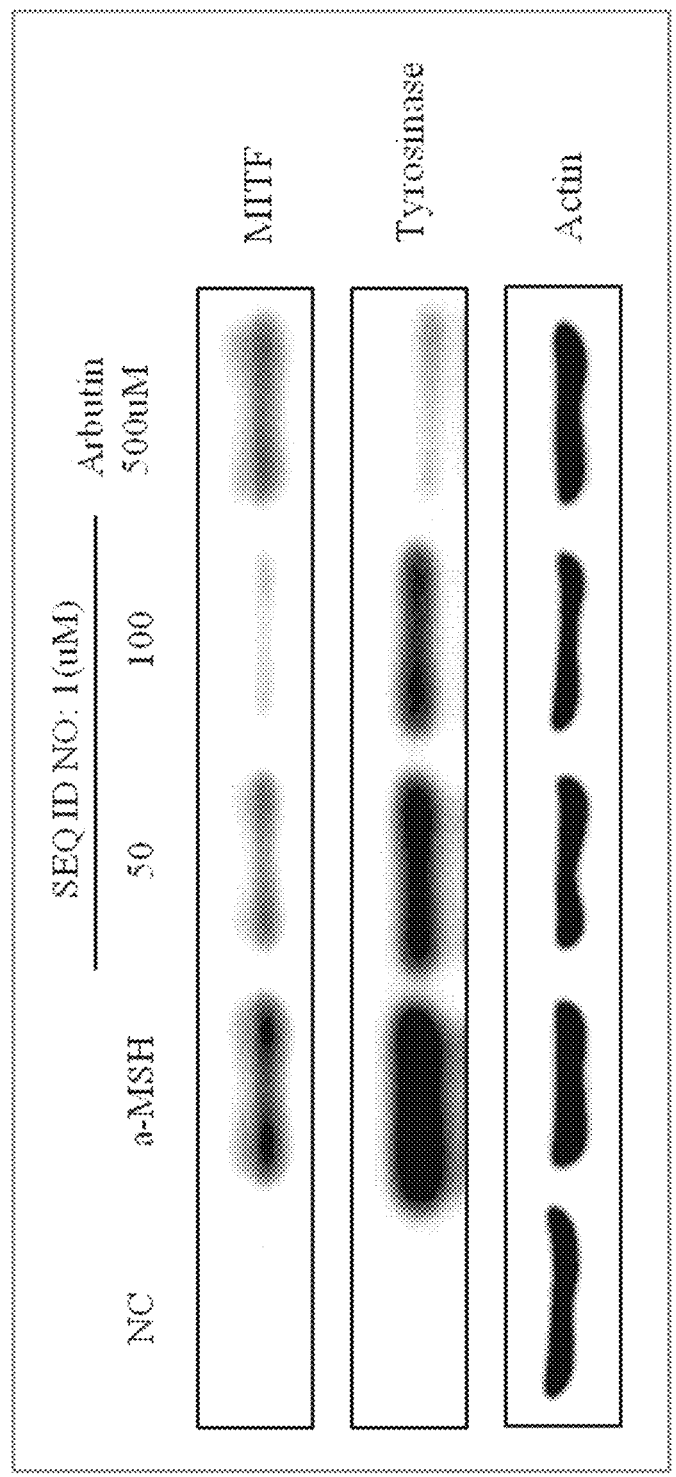
FIG. 7 provides images showing results of confirming changes in the protein expression of melanogenesis factors using antibodies specific to proteins of the melanogenesis factors when melanoma cell line (B16F10) was treated with a peptide according to an embodiment of the present invention.

As can be seen from FIG. 7, the MITF and tyrosinase protein expression inhibitory effects of the peptide consisting of a peptide having valproic acid bound to the N-terminus of the amino acid sequence of SEQ ID NO: 1 in a dose-dependent manner was verified.

Example 8: Observation of Melanogenesis Signaling Material

After melanin-forming cells (B16F10 cell line) were incubated in 6-well culture plates for 24 hours, the cells were treated with α-MSH (200 ng/ml) or the present peptide at different concentrations (50, 100 uM). After the cells were incubated for 10 minutes, the cells were lysed, and the degree of phosphorylation of CREB, which is a signaling material involved in melanogenesis, was observed using a western blot method using a specific antibody (Santa Cruz Biotechnology, USA). The results are shown in FIG. 8.

Figure 8:
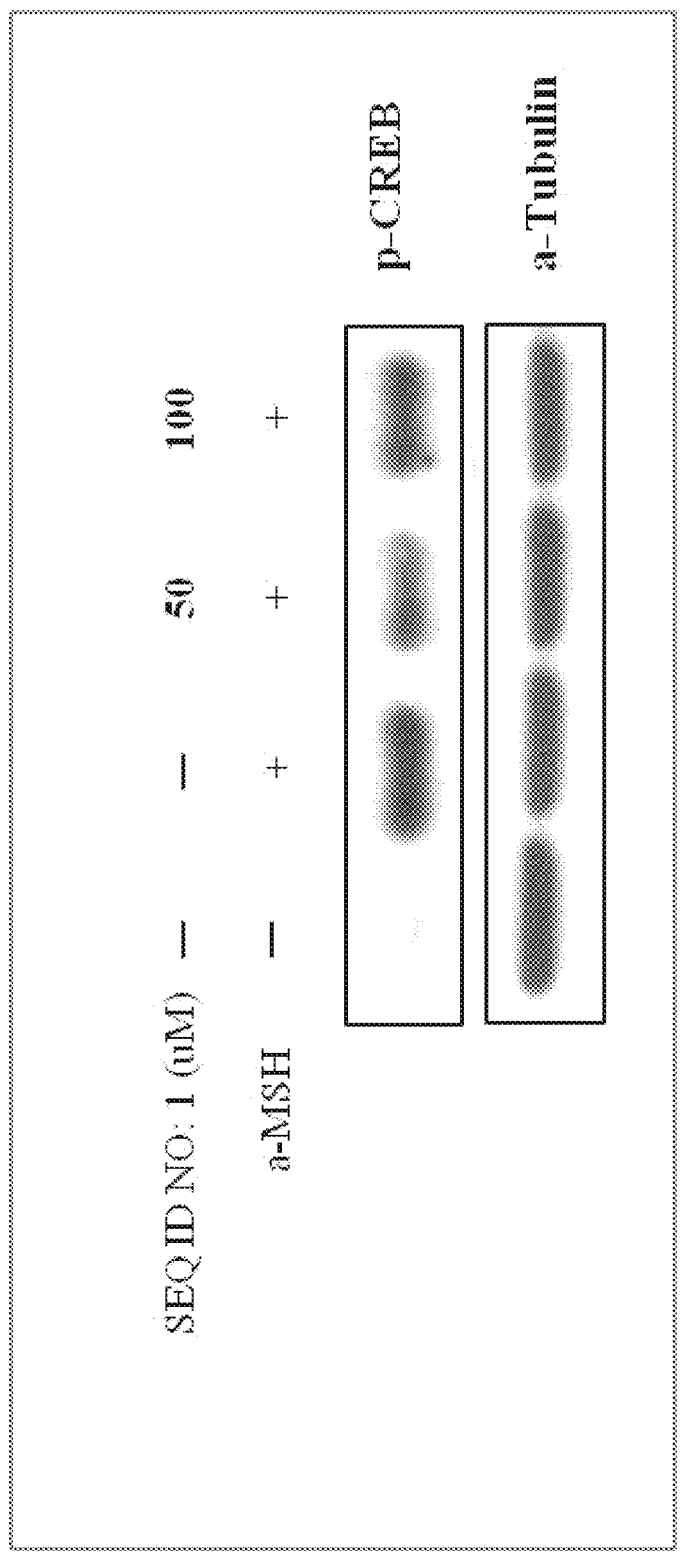
FIG. 8 provides images showing the results of confirming the degree of phosphorylation of CREB, which is a melanogenesis factor signaling material, when melanoma cell line (B16F10) was treated with a peptide according to an embodiment of the present invention.

As can be seen from FIG. 8, the CREB phosphorylation inhibitory effect of the peptide consisting of a peptide having valproic acid bound to the N-terminus of the amino acid sequence of SEQ ID NO: 1 was verified.

Through the above results, the peptide consisting of a peptide having valproic acid bound to the N-terminus of the amino acid sequence of SEQ ID NO: 1 inhibits the MC1R signaling pathway activated by α-MSH, thereby exhibiting a melanogenesis inhibitory effect.

Example 9: Observation of Change in Expression of Gene Involved in Activity and Phagocytosis of Keratinocytes After a human keratinocyte line (HaCaT) was incubated in 6-well culture plates for 24 hours, the cells were treated with trypsin (Trypsin 4 Unit, Soybean trypsin inhibitor 10 Unit) as an activity-inducing material and the present peptide at different concentrations (100, 200 uM). After RNA was extracted from the cells incubated for 16 hours, cDNA was prepared.

PCR was conducted using a primer pair (see table 3 below) specific to PAR2, which is one of surface receptors of keratocytes activated by a trypsin action, and then the change in the expression of each gene was observed. The results are shown in FIG. 9.

TABLE 3

| SEQ ID NO | Name | Sequence listing (5'→3') | Note |
|---|---|---|---|
| 6 | PAR2_F | TGCTAGCAGCCTC TCTCTCC | Annealing temperature, 60° C. |
| 7 | PAR2_R | CTTCAAGGGGAAC CAGATGA | |

Figure 9:
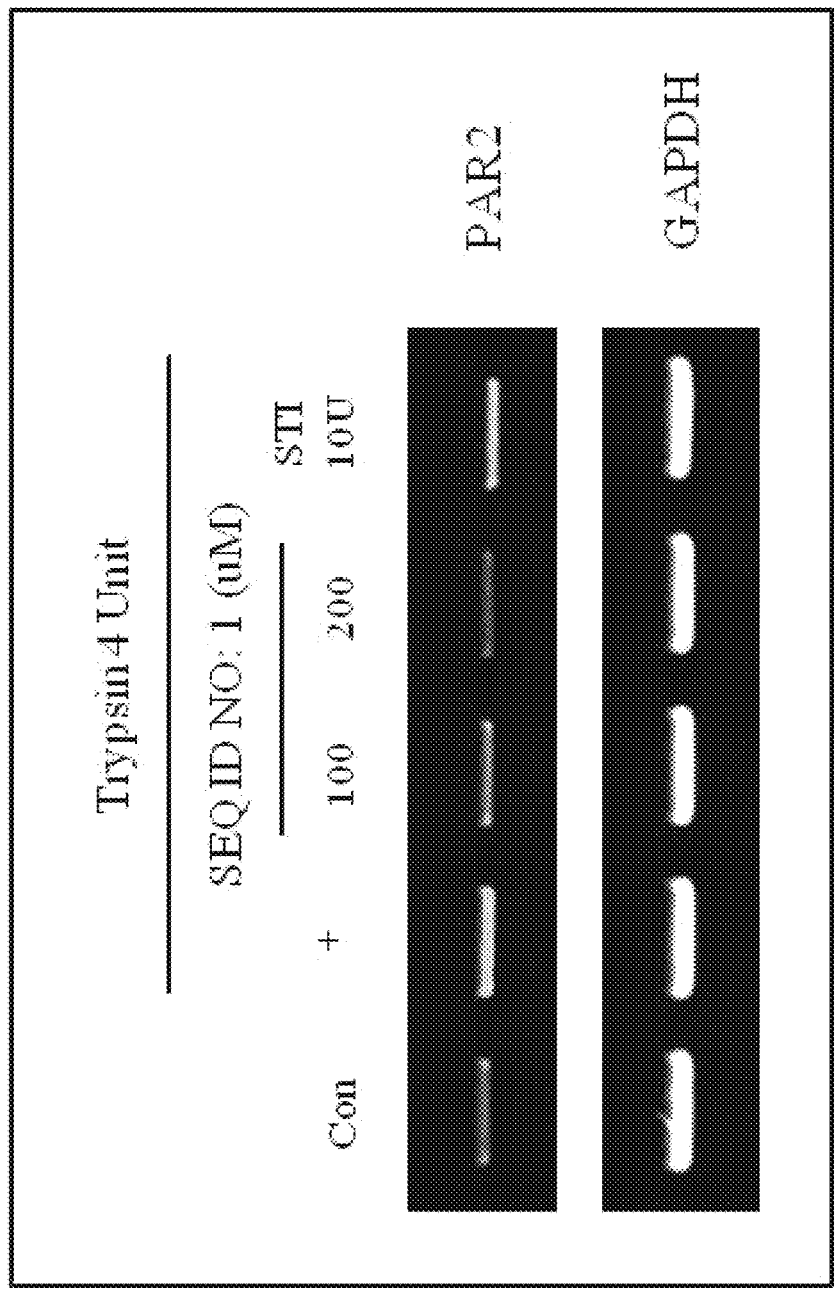
FIG. 9 provides images showing PCR results of confirming the change in the expression of a gene involved in the activity and phagocytosis of keratinocytes when human keratinocyte cell line (HaCat) was treated with a peptide according to an embodiment of the present invention.

As can be seen from FIG. 9, the gene expression was induced by the activation of PAR2 of keratocytes resulting from the treatment with trypsin as serine protease, and it was observed that the treatment with the peptide consisting of a peptide having valproic acid bound to the N-terminus of the amino acid sequence of SEQ ID NO: 1 reduced the expression of PAR2 gene in a dose-dependent manner.

Example 10: Verification of Inhibition of Melanosome Transfer into Keratinocytes (Using Isolated Melanosomes)

After human keratinocyte line (HaCaT) was cultured in 6-well culture plates for 24 hours, the melanosomes isolated from mouse melanoma cell line (B16F10) were pretreated for 3 hours in serum-free culture medium, and then the cells were treated with the present peptide at different concentrations (10, 50, 100, 200 uM) or arbutin (200 uM) as a positive control, followed by incubation for 48 hours. Then, the plates were washed with PBS to remove un-transferred melanosomes, and 1 N NaOH was added to pellets, which had been obtained through cell collection and precipitation. Then, 1 M NaOH was added to the pellets, and the pellets were dissolved in an oven at 80° C., and then the OD value at 490 nm was measured. In order to observe the melanosome transfer inhibitory effect of the peptide consisting of a peptide having valproic acid bound to the N-terminus of the amino acid sequence of SEQ ID NO: 1 according to the concentration, a keratinocyte phagocytosis assay was performed using the melanosomes isolated from melanoma. The results are shown in FIG. 10.

Figure 10:
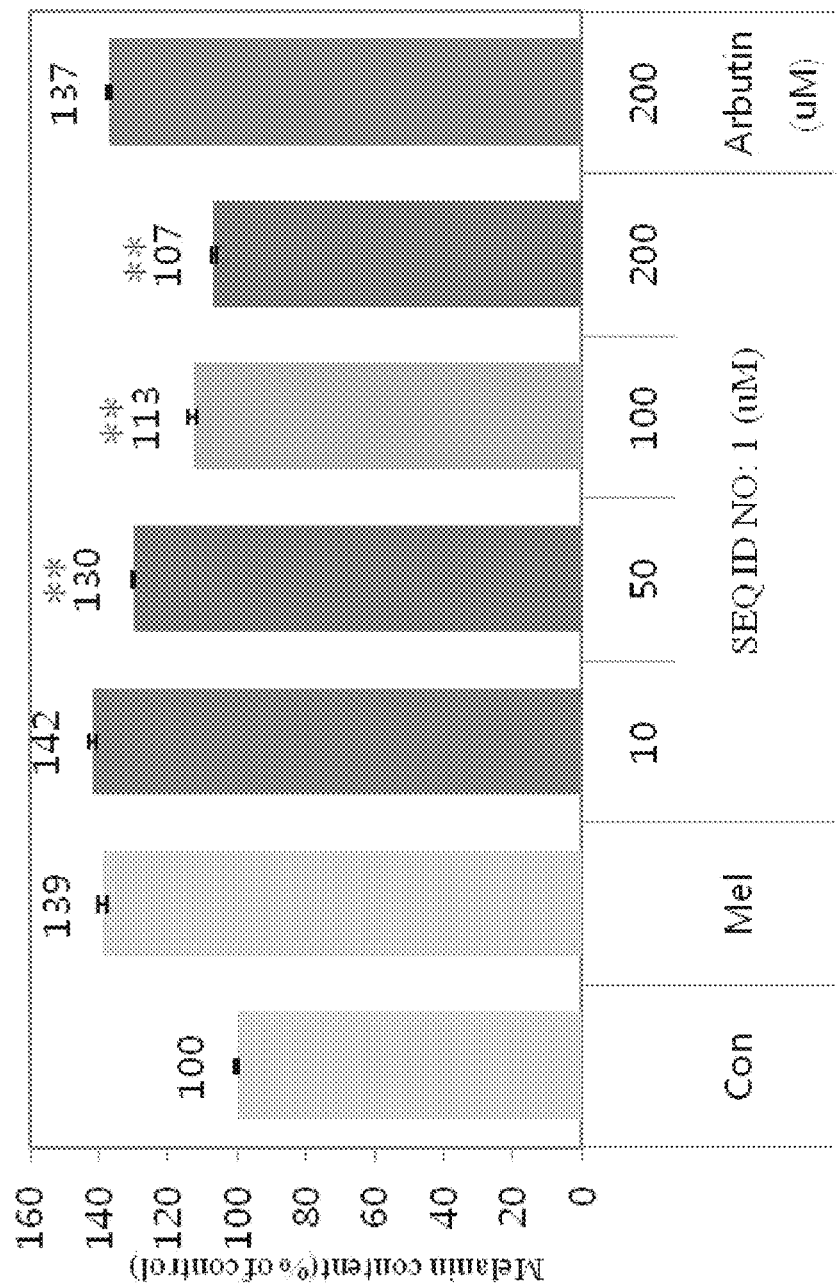
FIG. 10 is a graph showing the results of confirming the inhibition of melanosome transfer into keratinocytes when human keratinocyte cell line (HaCat) was treated with a peptide according to an embodiment of the present invention.

As can be seen from FIG. 10, as a result of examining the amount of melanosomes transferred into keratinocytes through the measurement of absorbance, the phagocytosis inhibitory effect of the peptide consisting of a peptide having valproic acid bound to the N-terminus of the amino acid sequence of SEQ ID NO: 1 in a dose-dependent manner was verified.

Example 11: Verification of Inhibition of Melanosome Transfer into Keratinocytes (Using Isolated Melanosomes)

After human keratinocyte line (HaCaT) was cultured in 6-well culture plates for 24 hours, the melanosomes isolated from mouse melanoma cell line (B16F10) were pretreated for 3 hours in serum-free culture medium. Then, the cells were treated with the present peptide at different concentrations (10, 50, 100, 200 uM) or arbutin (200 uM) as a positive control, followed by incubation for 48 hours. Then, the plates were washed with PBS to remove un-transferred melanosomes, and subjected to Fontana-Masson staining to observe the inhibition of the melanosome phagocytosis by keratinocytes through a microscope. In order to observe the melanosome transfer inhibitory effect of the peptide consisting of a peptide having valproic acid bound to the N-terminus of the amino acid sequence of SEQ ID NO: 1 according to the concentration, a keratinocyte phagocytosis assay was performed using melanosomes isolated from melanoma. The results are shown in FIG. 11.

Figure 11:
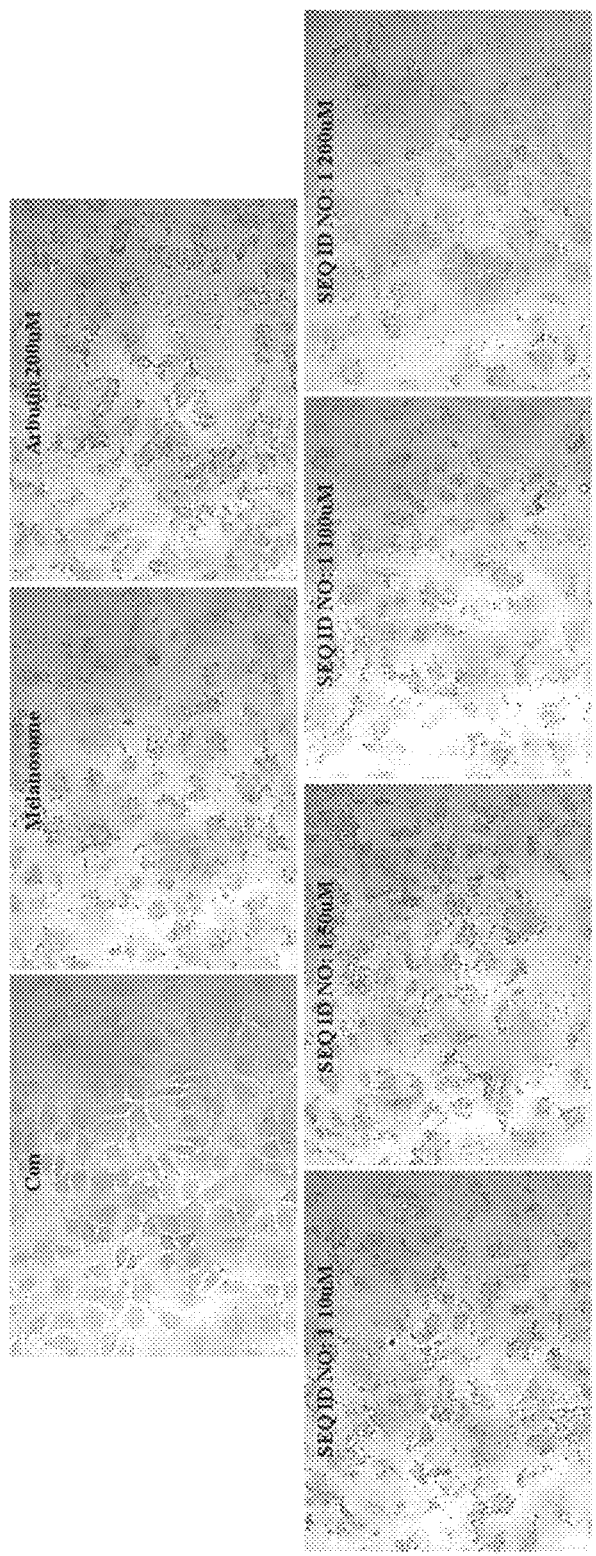
FIG. 11 provides images showing the results of confirming the inhibition of melanosome phagocytosis of keratinocytes when human keratinocyte cell line (HaCat) was treated with a peptide according to an embodiment of the present invention.

As can be seen from FIG. 11, as a result of examining the amount of melanosomes transferred into keratinocytes through optical microscope image analysis, the phagocytosis inhibitory effect of the peptide consisting of a peptide having valproic acid bound to the N-terminus of the amino acid sequence of SEQ ID NO: 1 in a dose-dependent manner was verified.

Example 12: Verification of Inhibition of Melanosome Transfer into Keratinocytes (Using Bioparticles)

After human keratinocyte line (HaCaT) was cultured in 24-well culture plates for 24 hours, the cells were treated with the present peptide at different concentrations (100, 200 uM) or arbutin (200 uM) as a positive control in 0.5% FBS culture medium, followed by incubation for 24 hours. Thereafter, the inhibition of phagocytosis of the human keratinocyte line was observed using the Vybrant Phagocytosis Assay Kit (V-6694). In order to observe the melanosome transfer inhibitory effect of the peptide consisting of a peptide having valproic acid bound to the N-terminus of the amino acid sequence of SEQ ID NO: 1 according to the concentration, a keratinocyte phagocytosis assay was performed using fluorescent-conjugated bioparticles. The results are shown in FIG. 12.

Figure 12:
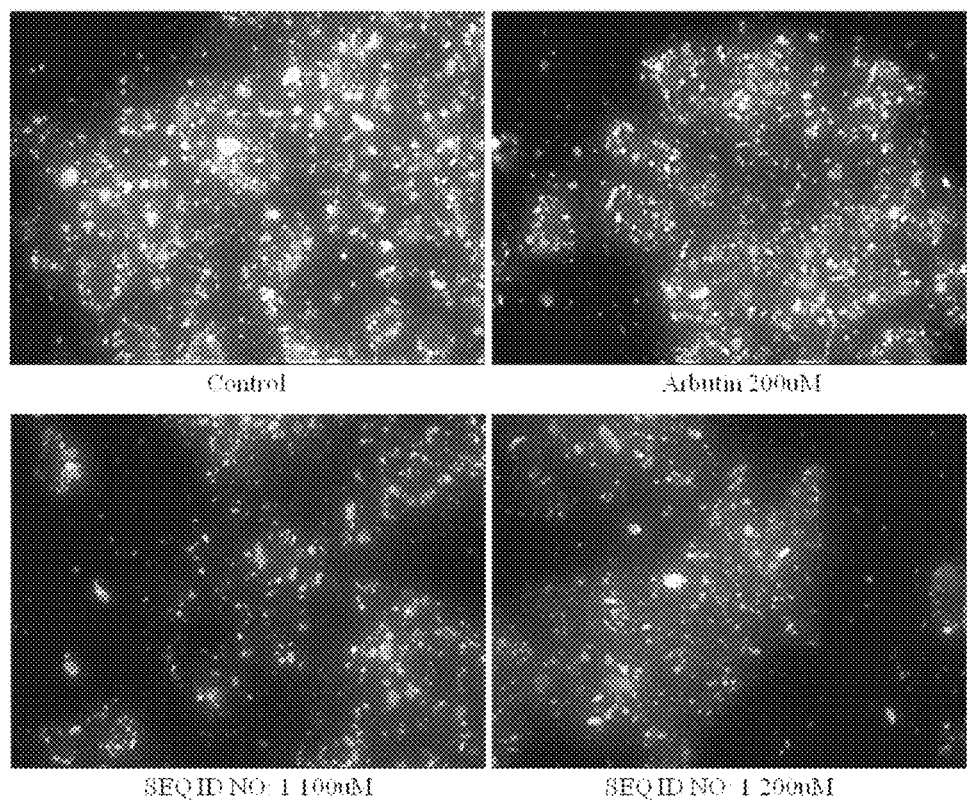
FIG. 12 provides images showing the results of a keratinocyte phagocytosis assay using fluorescent-conjugated bioparticles in order to observe the melanosome transfer inhibitory effect according to an embodiment of the present invention.

As can be seen from FIG. 12, as a result of examining the amount of bioparticles transferred into keratinocytes through fluorescent microscopic image analysis, the phagocytosis inhibitory effect of the peptide consisting of a peptide having valproic acid bound to the N-terminus of the amino acid sequence of SEQ ID NO: 1 in a dose-dependent manner was verified.

Example 13: Observation of Melanosome Degradation Ability in Keratinocytes

After human keratinocyte line (HaCaT) was cultured in 6-well culture plates for 24 hours, melanosomes isolated from mouse melanoma cell line (B16F10) were pretreated for 48 hours in serum-free culture medium. The plates were washed with PBS to remove un-transferred melanosomes, and then the cells were treated with the peptide at different concentrations (100, 200 uM) or arbutin (200 uM) as a positive control, and TGFβ-1, followed by incubation for 48 hours. In order to measure the degradation of melanosomes phagocytized into keratinocytes, 1 M NaOH was added to pellets obtained by keratinocyte collection and precipitation, and the pellets were dissolved in an oven at 80° C., and then the OD value at 490 nm was measured. The results are shown in FIG. 13.

Figure 13:
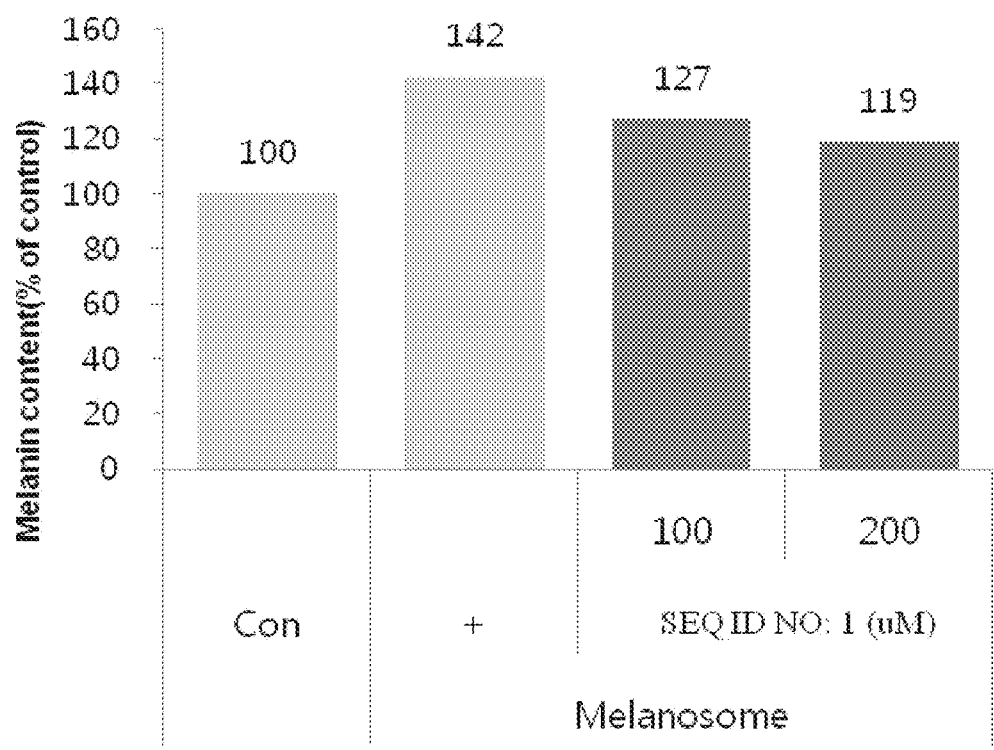
FIG. 13 is a graph showing the results of confirming the melanosome degradation ability in keratinocytes when human keratinocyte cell line (HaCat) was treated with a peptide according to an embodiment of the present invention.

As can be seen from FIG. 13, as a result of observing the effect of the peptide consisting of a peptide having valproic acid bound to the N-terminus of the amino acid sequence of SEQ ID NO: 1 to promote the degradation of the melanosomes transferred into the keratinocytes, the effect in a dose-dependent manner was verified.

Example 14: Observation of In Vivo Whitening Effect

Liposomal peptide (5,000 ppm) or arbutin as a positive control was applied to the tail of 8-week-old C57BL/6 mice once a day, and the experiment was conducted for about 8 weeks. After the completion of the experiment, the mice were sacrificed to extract tail skin tissues, which were then embedded in paraffin to manufacture paraffin blocks. Then, the paraffin blocks were made into paraffin sections and morphologically observed through Fontana-Masson staining. The results are shown in FIGS. 14a to 14c.

Figure 14A:
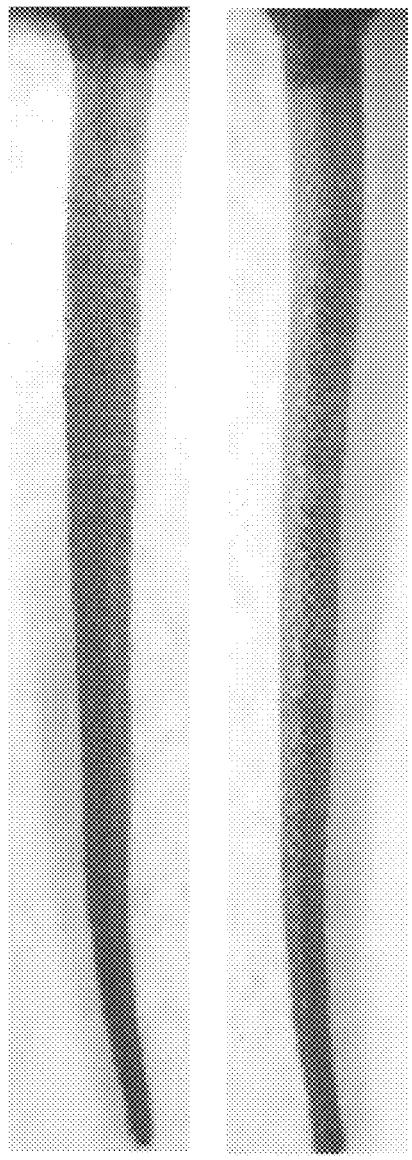
FIG. 14a provides an image showing results of observation of the in vivo whitening effect when a peptide according to an embodiment of the present invention was liposomized and applied to the tail of C57BL/6 mice.

As can be seen from FIG. 14a, as a result of the 8-week application experiment, it was observed that the tail color in the group treated with the liposomes including the peptide consisting of a peptide having valproic acid bound to the N-terminus of the amino acid sequence of SEQ ID NO: 1 was brighter than the tail color in the control group.

Figure 14B:
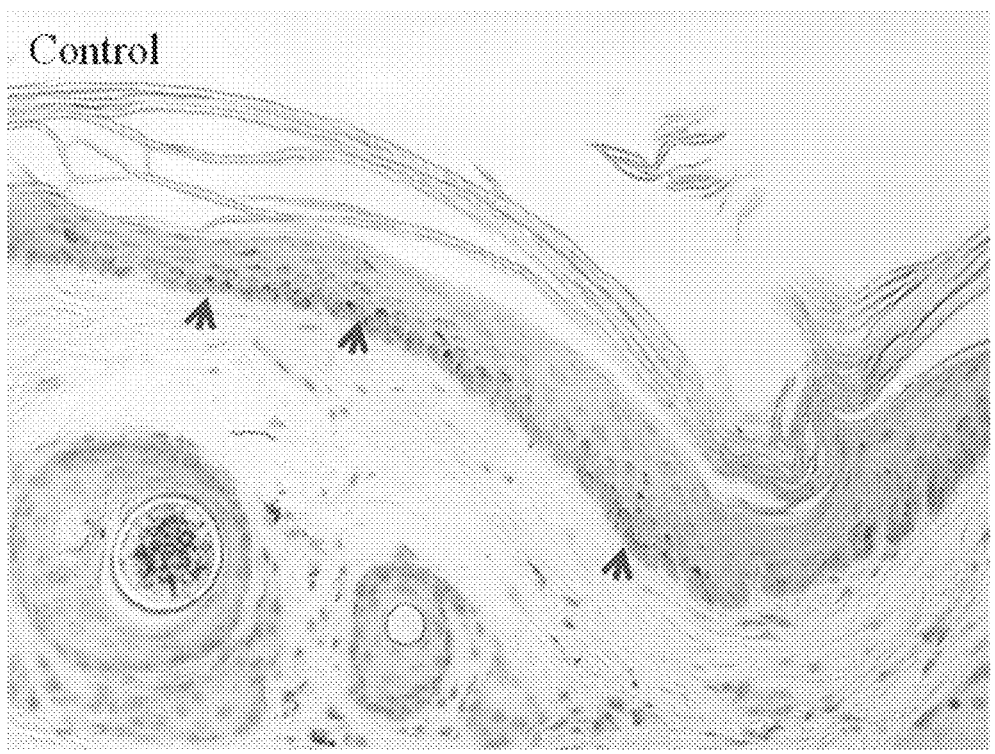
FIG. 14b provides an image showing results (comparative example) of observation of the in vivo whitening effect when a peptide according to an embodiment of the present invention was liposomized and applied to the tail of C57BL/6 mice.
Figure 14C:
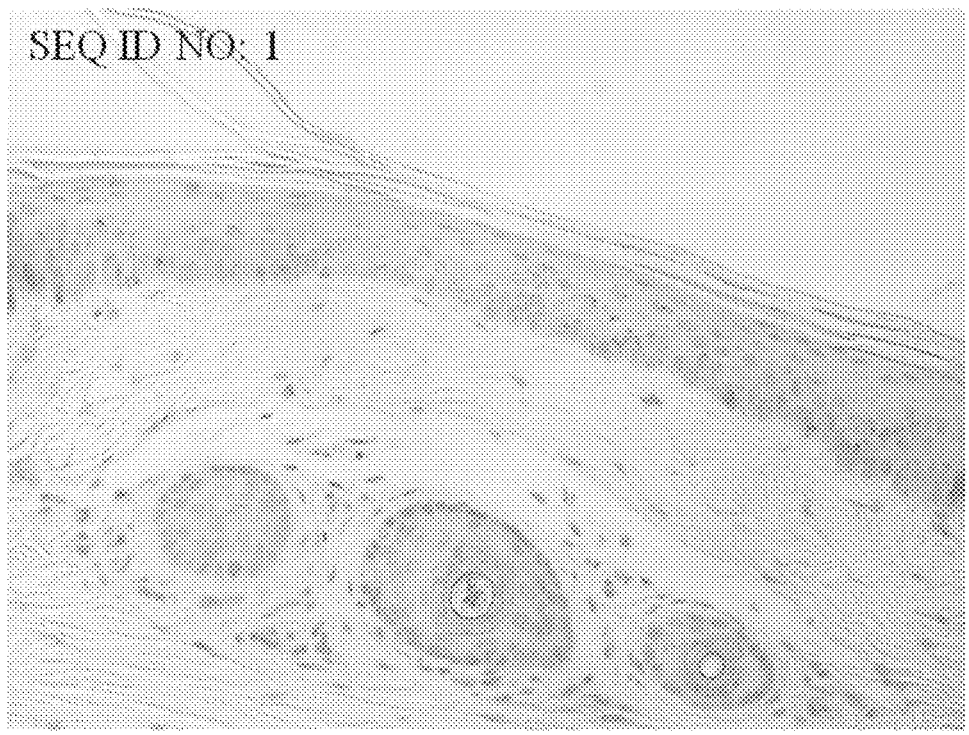
FIG. 14c provides an image showing results (example) of observation of the in vivo whitening effect when a peptide according to an embodiment of the present invention was liposomized and applied to the tail of C57BL/6 mice.
Figure 15A:
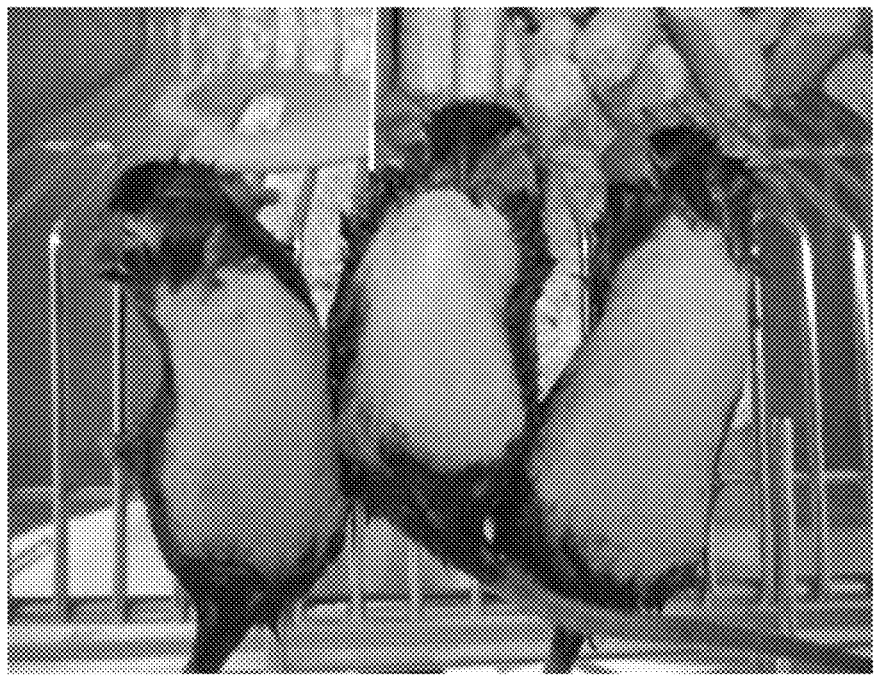
FIGS. 15a, 15b, 15c, 15d, 15e, and 15f are images showing results of observation of hair growth rates on day 0, 7, 10, 13, 15, and 17 after a peptide according to an embodiment of the present invention was liposomized and applied to the dorsal skin of C57BL/6 mice, from which the hairs had been removed.
Figure 15A:
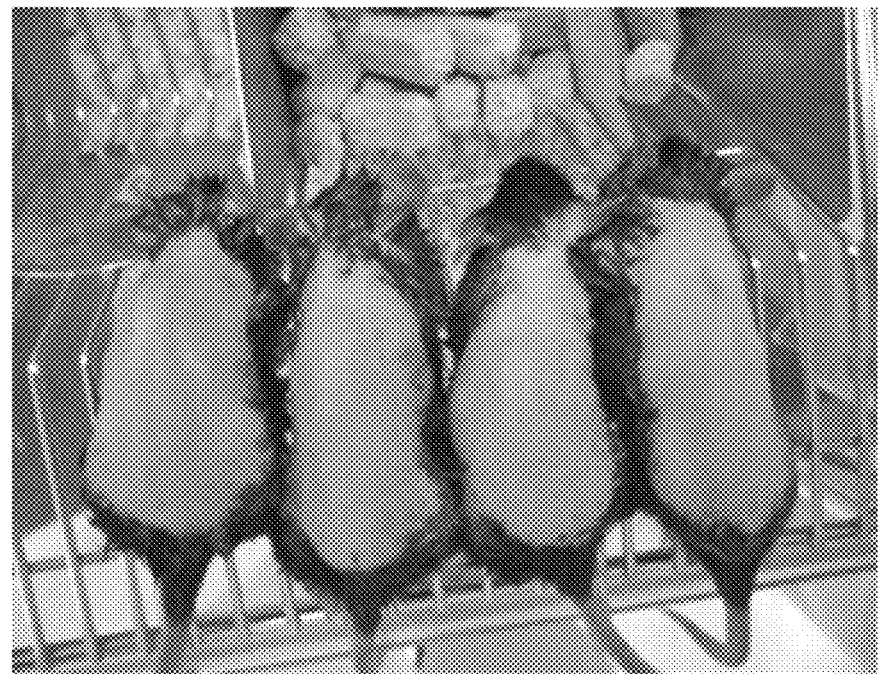
Figure 15B:
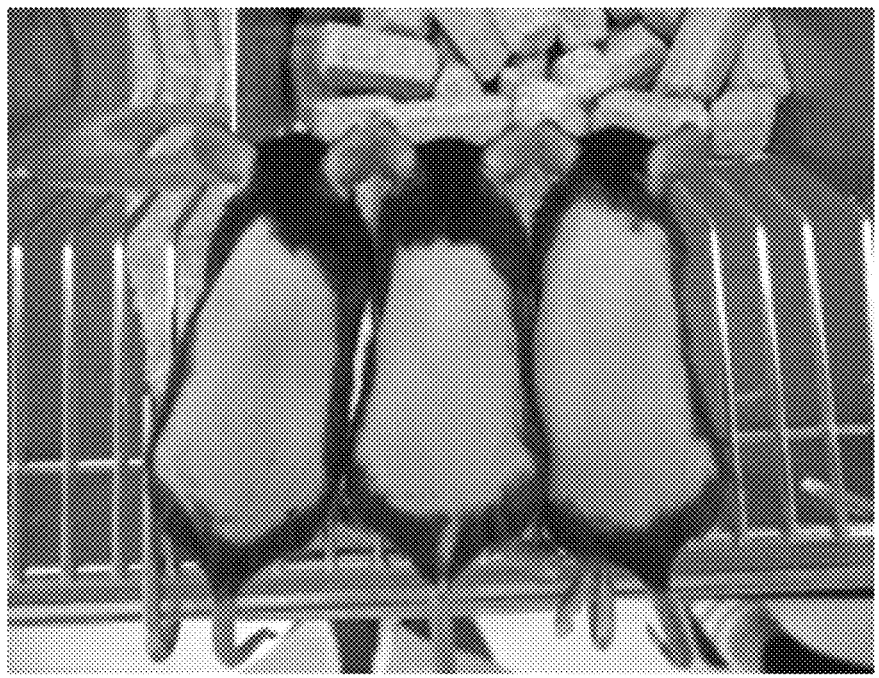
Figure 15B:
Figure 15C:
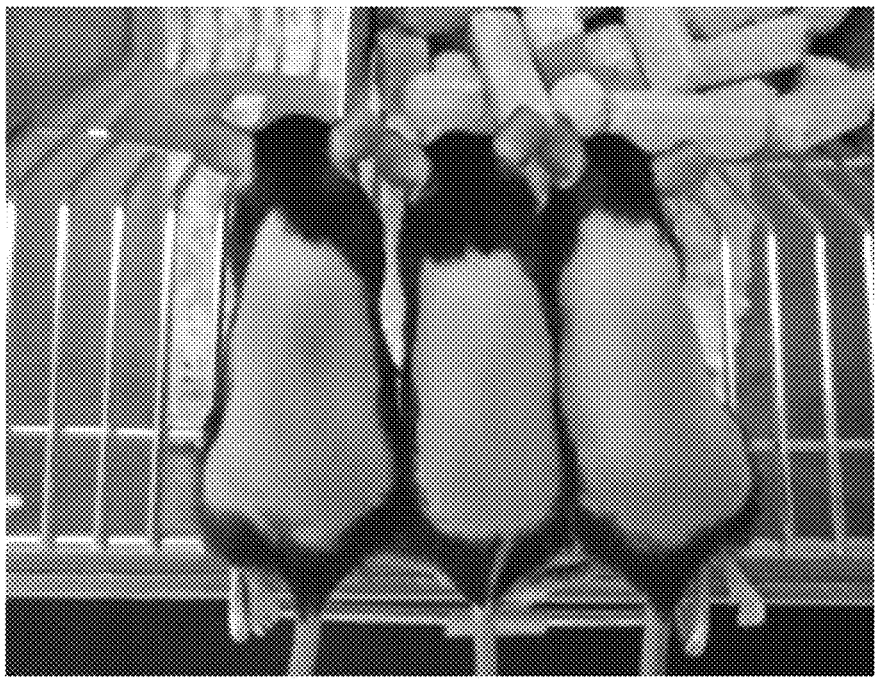
Figure 15C:
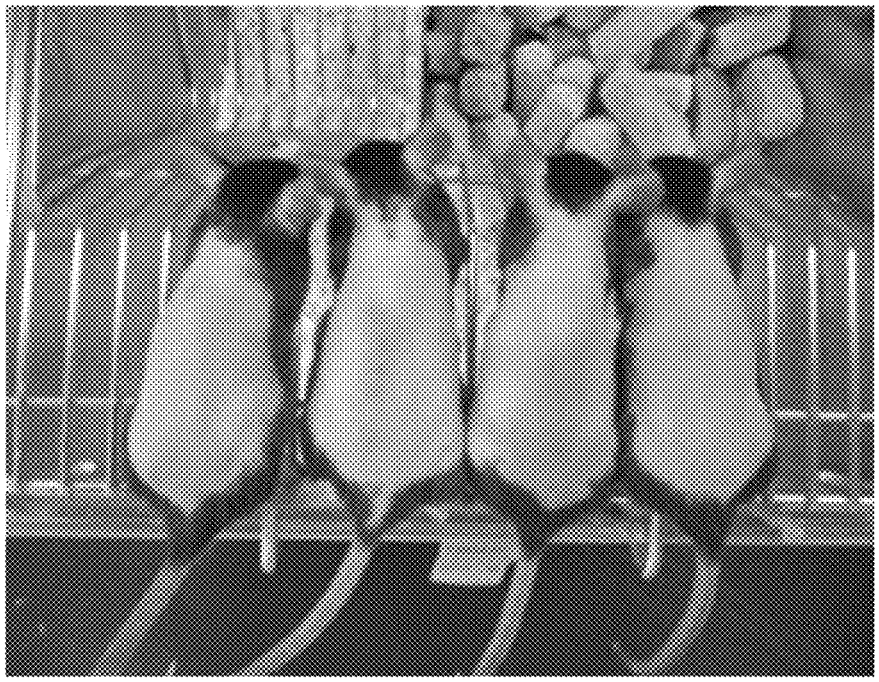
Figure 15D:
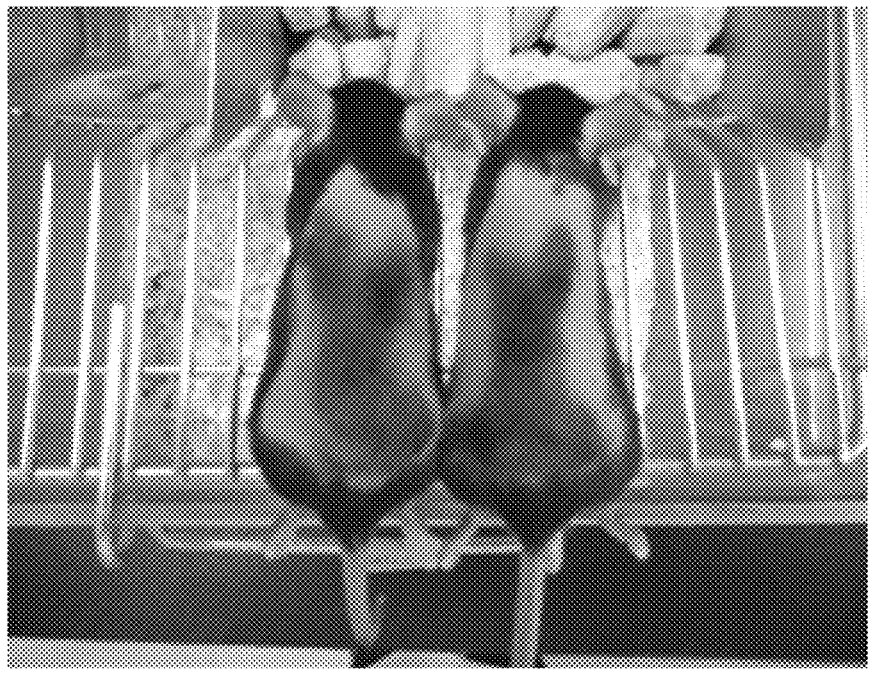
Figure 15D:
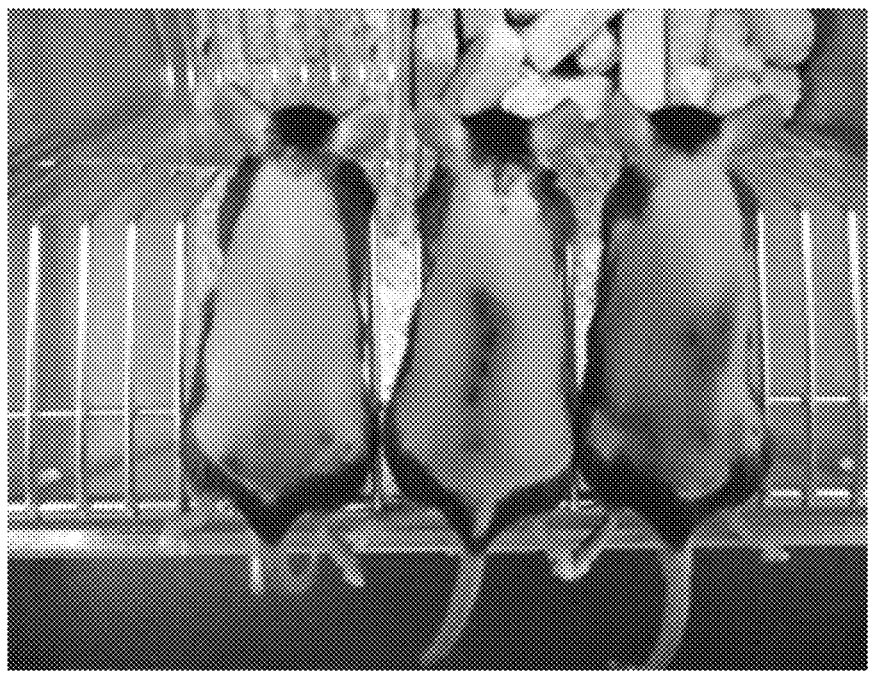
Figure 15E:
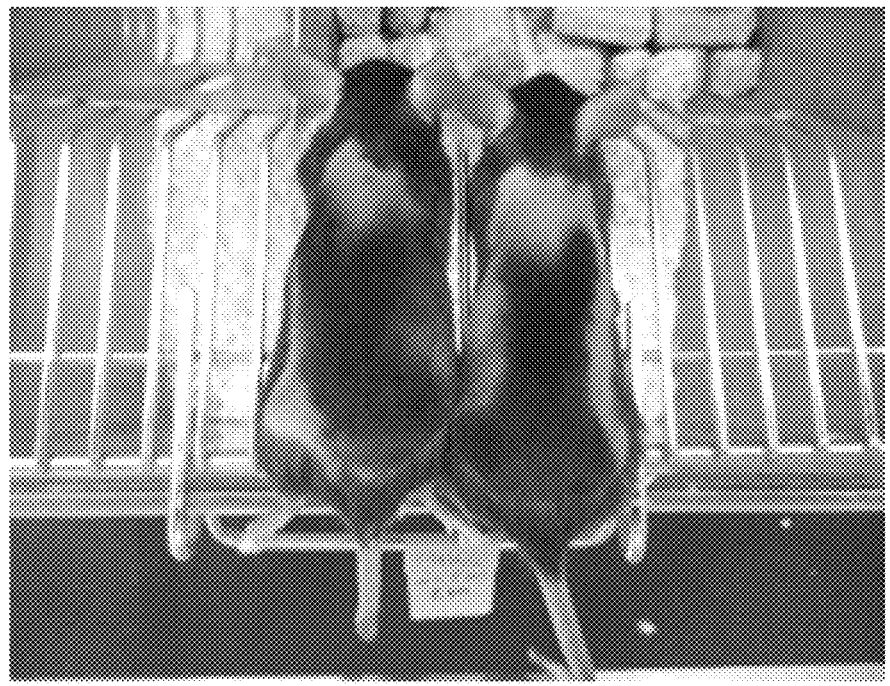
Figure 15E:
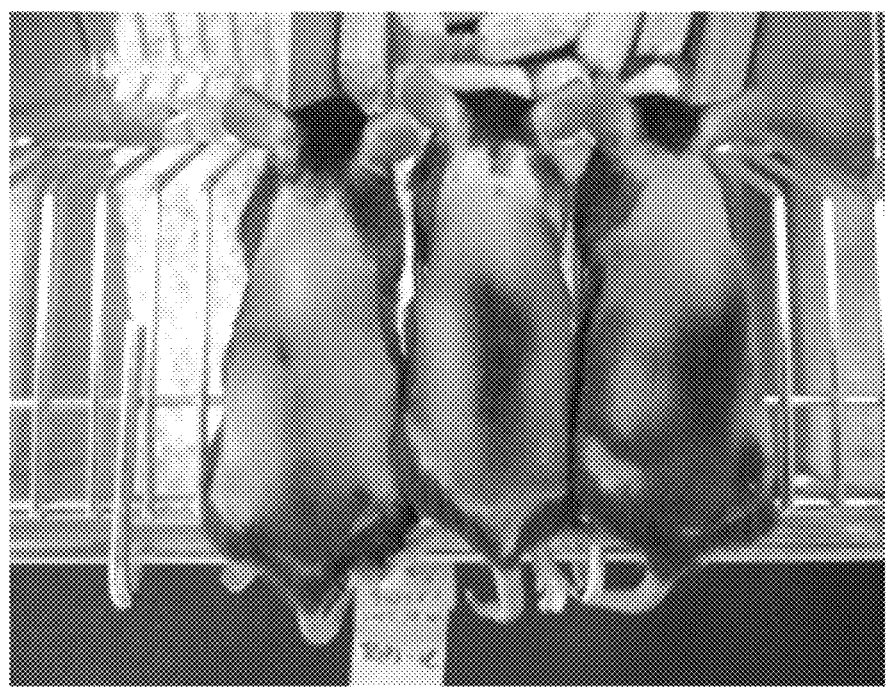
Figure 15F:
Figure 15F:

In addition, as can be seen from results of confirmation of melanin distribution through F&M staining in FIGS. 14b and 14c, it can be verified that the amount of melanin distributed in the basal layer of the epidermis in the group treated with the peptide consisting of a peptide having valproic acid bound to the N-terminus of the amino acid sequence of SEQ ID NO: 1 was much smaller than that in the control group.

Example 15: Observation of In Vivo Hair Growth Inhibition

The hairs on the dorsal skin of 8-week-old C57BL/6 mice were removed through waxing, and the liposomal peptides were applied thereto once a day for 17 days to observe the hair growth rate. The results are shown in FIG. 15.

As can be seen from FIG. 15, as a result of applying the liposomes including the peptide consisting of a peptide having valproic acid bound to the N-terminus of the amino acid sequence of SEQ ID NO: 1 on the dorsal skin of the mice, from which the hairs had been removed through waxing or the like, for 17 days, the hair growth rate was found to be distinctively slower compared with the control group.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A peptide having the amino acid sequence of SEQ ID NO: 1, wherein valproic acid is bound to the N-terminus of the amino acid sequence.

2. A composition comprising an effective amount of the peptide of claim 1 and at least one excipient.

3. A method for whitening skin comprising:
administering to a subject in need thereof an effective amount of the peptide of claim 1.

4. The method of claim 3, wherein the peptide inhibits melanogenesis.

5. The method of claim 3, wherein the peptide inhibits the activity of tyrosinase.

6. The method of claim 3, wherein the peptide inhibits the expression of a melanogenesis-involved factor.

7. The method of claim 6, wherein the melanogenesis-involved factor is microphthalmia-associated transcription factor (MITF) or proteinase-activated receptor 2 (PAR2).

8. The method of claim 3, wherein the peptide inhibits the phosphorylation of cAMP response element-binding protein (CREB) which is a signaling material involved in melanogenesis.

9. The method of claim 3, wherein the peptide inhibits melanosome transfer.

10. The method of claim 3, wherein the peptide exhibits the ability to promote melanosome degradation.

11. A method for inhibiting hair growth comprising:
administering to a subject in need thereof an effective amount of the peptide of claim 1.

12. The method of claim 11, wherein the peptide inhibits melanogenesis.

13. The method of claim 11, wherein the peptide inhibits the activity of tyrosinase.

14. The method of claim 11, wherein the peptide inhibits the expression of a melanogenesis-involved factor.

15. The method of claim 14, wherein the melanogenesis-involved factor is microphthalmia-associated transcription factor (MITF) or proteinase-activated receptor 2 (PAR2).

16. The method of claim 11, wherein the peptide inhibits the phosphorylation of cAMP response element-binding protein (CREB) which is a signaling material involved in melanogenesis.

17. The method of claim 11, wherein the peptide inhibits melanosome transfer.

18. The method of claim 11, wherein the peptide exhibits the ability to promote melanosome degradation.

* * * * *

SEQUENCE LISTING

<160> NUMBER OF SEQ ID NOS: 7

<210> SEQ ID NO 1
<211> LENGTH: 13
<212> TYPE: PRT
<213> ORGANISM: Artificial
<220> FEATURE:
<223> OTHER INFORMATION: Apigmerin

<400> SEQUENCE: 1

Ile Trp Ser Leu Asp Thr Gln Tyr Gly Gly Arg Gly Asp
1               5                   10

<210> SEQ ID NO 2
<211> LENGTH: 21
<212> TYPE: DNA
<213> ORGANISM: Artificial
<220> FEATURE:
<223> OTHER INFORMATION: MITF Forward Primer

<400> SEQUENCE: 2
ccagcctggc gatcatgtca t                                          21

<210> SEQ ID NO 3
<211> LENGTH: 20
<212> TYPE: DNA
<213> ORGANISM: Artificial
<220> FEATURE:
<223> OTHER INFORMATION: MITF Reverse Primer

<400> SEQUENCE: 3
ggtctggaca ggagttgctg                                            20

<210> SEQ ID NO 4
<211> LENGTH: 20
<212> TYPE: DNA
<213> ORGANISM: Artificial
<220> FEATURE:
<223> OTHER INFORMATION: Tyrosinase Forward Primer

<400> SEQUENCE: 4
ggccagcttt caggcagagg                                            20

<210> SEQ ID NO 5
<211> LENGTH: 20
<212> TYPE: DNA
<213> ORGANISM: Artificial
<220> FEATURE:
<223> OTHER INFORMATION: Tyrosinase Reverser Primer

<400> SEQUENCE: 5
tggtgcttca tgggcaaaat                                            20

<210> SEQ ID NO 6
<211> LENGTH: 20
<212> TYPE: DNA
<213> ORGANISM: Artificial
<220> FEATURE:
<223> OTHER INFORMATION: PAR2 Forward Primer

<400> SEQUENCE: 6
tgctagcagc ctctctctcc                                            20

<210> SEQ ID NO 7
<211> LENGTH: 20
<212> TYPE: DNA

```
<213> ORGANISM: Artificial
<220> FEATURE:
<223> OTHER INFORMATION: PAR2 Reverse Primer

<400> SEQUENCE: 7
cttcaagggg aaccagatga                                        20
```